(12) United States Patent
Zhang

(10) Patent No.: US 12,385,938 B2
(45) Date of Patent: Aug. 12, 2025

(54) SAMPLE DILUTION METHOD AND IMMUNOASSAY METHOD

(71) Applicant: SHENZHEN INCRECARE BIOTECH CO. LTD, Shenzhen (CN)

(72) Inventor: Zhen Zhang, Shenzhen (CN)

(73) Assignee: SHENZHEN INCRECARE BIOTECH CO. LTD (CN)

(*) Notice: Subject to any disclaimer, the term of this patent is extended or adjusted under 35 U.S.C. 154(b) by 1017 days.

(21) Appl. No.: 17/427,883

(22) PCT Filed: Apr. 11, 2019

(86) PCT No.: PCT/CN2019/082178
§ 371 (c)(1),
(2) Date: Aug. 2, 2021

(87) PCT Pub. No.: WO2020/155389
PCT Pub. Date: Aug. 6, 2020

(65) Prior Publication Data
US 2022/0120772 A1      Apr. 21, 2022

(30) Foreign Application Priority Data

Feb. 2, 2019 (CN) .......................... 201910107354.9

(51) Int. Cl.
*G01N 35/10* (2006.01)
*G01N 1/38* (2006.01)
(Continued)

(52) U.S. Cl.
CPC ........... *G01N 35/1002* (2013.01); *G01N 1/38* (2013.01); *G01N 33/531* (2013.01); *G01N 35/0092* (2013.01); *G01N 2035/00465* (2013.01)

(58) Field of Classification Search
None
See application file for complete search history.

(56) References Cited

U.S. PATENT DOCUMENTS 5,882,594 A * 3/1999 Kawaguchi .......... G01N 35/025
422/65
6,786,235 B2   9/2004 Liang
(Continued)

FOREIGN PATENT DOCUMENTS

CN      1826218 A    8/2006
CN    101675170 A    3/2010
(Continued)

OTHER PUBLICATIONS

International Search Report for PCT/CN2019/082178 with English Translation mailed Nov. 1, 2019, 5 pages.

*Primary Examiner* — P. Kathryn Wright
(74) *Attorney, Agent, or Firm* — Dickinson Wright PLLC

(57) ABSTRACT

A sample dilution method. The method comprises the following steps: moving from an initial workstation to a first workstation a ferrying unit bearing a first reactor containing a sample; distributing a diluent into the first reactor located at the first workstation; mixing the diluent and the sample in the first reactor to form a diluted sample; moving to a second workstation the ferrying unit bearing the first reactor containing the diluted sample, and distributing into at least two empty second reactors the diluted sample from the first reactor; moving to the first workstation the ferrying unit bearing all the second reactors containing a diluted sample, and distributing a reagent into the second reactors located at the first workstation; and mixing the reagent and the diluted sample in the second reactor.

5 Claims, 11 Drawing Sheets

(51) Int. Cl.
*G01N 33/531* (2006.01)
*G01N 35/00* (2006.01)

(56) References Cited

U.S. PATENT DOCUMENTS

| | | |
|---|---|---|
| 6,947,126 B2 | 9/2005 | Grant et al. |
| 2003/0174306 A1 | 9/2003 | Grant et al. |

FOREIGN PATENT DOCUMENTS

| | | |
|---|---|---|
| CN | 201607358 U | 10/2010 |
| CN | 104076160 A | 10/2014 |
| CN | 104730268 A | 6/2015 |
| CN | 106645765 A | 5/2017 |
| CN | 106706942 A | 5/2017 |
| CN | 207816996 U | 9/2018 |
| CN | 207866716 U | 9/2018 |
| JP | H01257267 A | 10/1989 |
| JP | H052022 A | 1/1993 |
| JP | H1062432 A | 3/1998 |

\* cited by examiner

SAMPLE DILUTION METHOD AND IMMUNOASSAY METHOD

CROSS-REFERENCE TO RELATED APPLICATION

The present is a national phase application of International Application No. PCT/CN2019/082178, filed on Apr. 11, 2019, which claims the priority of the Chinese patent application filed with the Chinese Patent Office on Feb. 2, 2019, with the filing number of No. 201910107354.9, and the title of "Sample Dilution Method and Immunoassay Method," the entire contents thereof being incorporated herein by reference.

TECHNICAL FIELD

The present disclosure relates to the technical field of in-vitro diagnostics, in particular to a sample dilution method and an immunoassay method containing respective steps in the sample dilution method.

BACKGROUND ART

The full-automatic immunity analyzer can perform quantitative or qualitative detection on target analyte such as antibody and antigen contained in a sample to be tested such as blood. Generally, an empty reactor is dispensed with the sample to be tested and a reagent (or called as reactant), and after steps such as uniformly mixing, incubating, cleaning and separating (bound-free, i.e. BF separating), a signal reagent is dispensed into the reactor so as to measure an optical signal or an electrical signal, thus realizing measurement and analysis of the target analyte contained in the sample to be tested.

An important parameter for evaluating the operation efficiency of the immunity analyzer is test throughput, where the test throughput may be understood as the number of test results, i.e. the number of measured reactors containing the target analyte, that can be reported by the immunity analyzer in unit time, and the more the total number of reactors measured in unit time is, the higher the test throughput of the immunity analyzer is. As a reaction mode and a test flow of analytical items are usually different, the test throughput of the immunity analyzer is not unchanged, and the maximum test throughput is usually taken as the measurement standard of test speed of the immunity analyzer. In the present disclosure, for convenience of description, unless otherwise specified, the test throughput specifically refers to the maximum test throughput of the analyzer. The treatment of the immunity analyzer on the reactor is regarded as a pipeline, if N reactors containing the target analyte complete the measurement in unit time and leave the pipeline, in order to ensure that the test is performed continuously and reliably according to the maximum throughput, there also must be N empty reactors entering the pipeline within the same period of time, that is, a flow rate (inlet flow rate) of the reactor at an inlet of the pipeline is equal to a flow rate (outlet flow rate) at an outlet. By the same reasoning, in order to ensure seamless and continuous connection of the whole pipeline, the flow rate of the reactor in each stage of the pipeline should be equal to the inlet flow rate and the outlet flow rate, that is, the flow rate of the pipeline is equal everywhere.

Generally, before the sample and the reagent are uniformly mixed, the sample must be diluted first, while the dilution process takes more time, so that the flow rate of the reactor in the dilution stage is relatively low, thereby becoming a bottleneck and a shortcoming that affect the operation efficiency, and causing it difficult for the immunity analyzer to meet the requirements of higher test throughput.

SUMMARY

One technical problem solved by the present disclosure is how to improve the operation efficiency of a sample dilution method.

A sample dilution method, including the following steps:
moving a ferrying unit bearing a first reactor already containing a sample from an initial position to a first position;
dispensing a diluent into the first reactor located at the first position;
uniformly mixing the sample and the diluent in the first reactor so as to form a diluted sample;
moving the ferrying unit bearing the first reactor containing the diluted sample to a second position, and dispensing the diluted sample in the first reactor into at least two empty second reactors;
moving the ferrying unit bearing all the second reactors containing the diluted sample to the first position, and dispensing the reagent into the second reactors located at the first position; and
uniformly mixing the diluted sample and the reagent in the second reactors.

An immunoassay method, including the steps in the above sample dilution method.

BRIEF DESCRIPTION OF DRAWINGS

In order to more clearly illustrate technical solutions in embodiments of the present disclosure or the prior art, accompanying drawings which need to be used in the description of the embodiments or the prior art will be introduced briefly below, and apparently, the accompanying drawings in the description below merely show some embodiments of the present disclosure, and those ordinarily skilled in the art still could obtain other accompanying drawings in light of these accompanying drawings, without using inventive efforts.

DETAILED DESCRIPTION OF EMBODIMENTS

Figure 1:
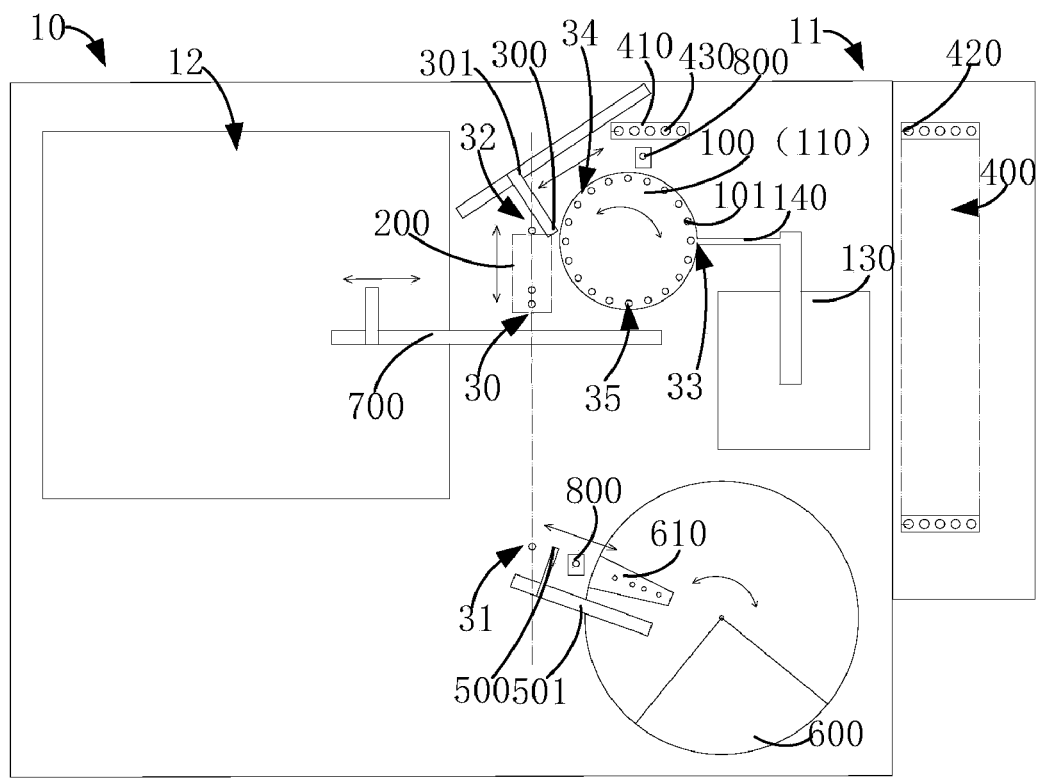
FIG. 1 is a plane structural schematic view of a first exemplary immunity analyzer provided in a first embodiment.

In order to facilitate understanding the present disclosure, the present disclosure will be described more comprehensively below with reference to relevant accompanying drawings. Preferred embodiments of the present disclosure are given in the accompanying drawings. However, the present disclosure may be implemented in many different forms, but not limited to the embodiments described herein. In contrast, these embodiments are provided for the purpose of making the contents disclosed in the present disclosure more thorough and more comprehensive.

It should be noted that when an element is "fixed to" another element, it may be directly on the another element or there may be an intermediate element therebetween. When an element is considered "connected to" another element, it may be directly connected to the another element or there may be an intermediate element therebetween. Terms used herein such as "inner", "outer", "left", "right" and the similar description are merely for illustrative purpose, rather than representing a unique embodiment.

Referring to FIG. 1 to FIG. 8 together, incubation of sample and reagent (or called as reactant) refers to a process of antigen-antibody binding reaction or biotin-avidin binding reaction of reactants in a reactor 20 in a constant temperature environment before bound-free is started. The reagent and analytical item herein are in a "one-to-one correspondence" relationship, that is, specific reagents corresponding to different analytical items are generally different in terms of formula, reagent volume, component quantity, and the like. Depending on different specific analytical items, the reagent typically includes multiple components, such as the usual 2-5 components, including reagent components such as magnetic particle, marker, diluent, and dissociating agent (respective corresponding reagent components may be represented by R1, R2, R3, and R4, respectively). For example, T4 reagent (thyroxine) includes three components, namely, magnetic particle (R1), marker (R2), and dissociating agent (R4). According to different reaction modes, multiple reagent components of one analytical item may be dispensed at one time or may be dispensed in multiple steps, and when the reagent components are dispensed in multiple steps, a first reagent, a second reagent, a third reagent, and so on are defined according to a dispensing order. After the incubation is completed, bound-free is carried out, where the bound-free refers to a process of capturing bound magnetic particles and labeled complexes with a magnetic field, and meanwhile removing free markers and other unreacted or unbound ingredients (unbound ingredients for short herein for convenience of description). After the bound-free, a signal reagent is dispensed to perform signal incubation (generally for 1-6 minutes), and finally a luminescence amount (reactant signal for short herein for convenience of expression) generated by reaction of a labeled reagent with the signal reagent is measured. The signal reagent is used for measuring the generation of signal (usually the luminescence amount), is usually a kind of common reagent, and has a "one-to-many" correspondence relationship with the analytical item, that is, different analytical items share one signal reagent. Signal incubation refers to a process of reacting in a constant temperature environment for a period of time after the signal reagent is dispensed into the reactor 20 after bound-free, to enhance the signal. It should be noted that, due to different specific components of the signal reagent, some luminous systems do not need signal incubation, and can directly measure in the process of dispensing the signal reagent or after dispensing the signal reagent. The signal reagent may be one or more, for example, some signal reagents include a first signal reagent, a second signal reagent, and so on. In an immunoassay device, the antigens or antibodies contained in the sample bound to the labeled reagent are quantitatively or qualitatively determined through the above process. Besides, an immunity analyzer 10 can perform an analysis corresponding to several different analytical items on a sample.

Operation period or cycle, period for short, is the shortest time window that can be cyclically reproduced in the test process, and it usually has a fixed length of time, and within the time of period, a certain number of process operations, tasks or work packages, and the like, such as operations and tasks of taking liquid, uniformly mixing, incubating, bound-free and measuring, are executed serially or in parallel in a controlled order. The tasks of the same component in one period are usually executed serially, and the tasks of different components in the same period may be executed serially or in parallel depending on whether actions of relevant components have a dependency relationship. All process operations executed in one period are executed only when needed, and not necessarily repeated in another period. In particular, some process operations may appear repeatedly in each period, while other process operations may occur every two or more periods. When multiple tests are performed in succession, since each test is usually at a different stage of the test procedure, among all process operations that occur in a single period, only some process operations are dedicated to executing a test, and other process operations are used for executing other tests. In order to improve the test efficiency and throughput, for components having a speed bottleneck, the number of components may be increased and the period of the components may be prolonged to improve the test efficiency and throughput, so that the operation periods of different components are not necessarily the same, that is, there may be multiple parallel periods in the same system. Generally, time lengths of multiple parallel periods have a multiple (fold) relationship, with the multiple usually being equal to the number of the same component. When there are two operation periods, they are called as a first period and a second period, respectively, for example, when the number of ferrying units 200 is N (N≥2, being a natural number), each ferrying unit 200 operates in the first period, the duration of the first period is N times that of the second period, and a sequences of actions of the N ferrying units 200 are continuously "in parallel in a manner of being staggered" by the second period.

It should be noted that not all components or operations run according to the operation period, while some components or operations, of which the operation processes have no effect on the test performance or test result, may not run according to a fixed period, for example, supply of the reactor 20 may not have a fixed operation period.

Referring to FIG. 1 to FIG. 5, the immunity analyzer 10 provided in an embodiment of the present disclosure includes a liquid dispensing device 11 and a reaction device 12, wherein the liquid dispensing device 11 is located beside the reaction device 12, and the liquid dispensing device 11 is configured to complete in the reactor 20 the dispensing of a sample and a reagent, and the uniform mixing of the sample and the reagent. The reaction device 12 is configured to perform incubation, bound-free, and measurement for the sample and the reagent (reactants) uniformly mixed in the reactor 20.

The liquid dispensing device 11 includes a buffer unit 100, a supply silo 130, a supply slide 140, a ferrying unit 200, a sample adding member 300, a sample conveying unit 400, a reagent dispensing member 500, a storage unit 600, a transfer unit 700, a washing tank 800, and a sorting mechanism. Certainly, the liquid dispensing device 11 may also include a sample adding drive unit 301 and a reagent drive unit 501, as well as a sample adding power device and a reagent dispensing power device, the sample adding member 300 is installed on the sample adding drive unit 301, and the sample adding drive unit 301 is configured to drive the sample adding member 300 to move so that the sample adding member 300 draws or discharges the sample under the action of the sample adding power device. The reagent dispensing member 500 is installed on the reagent drive unit 501, and the reagent drive unit 501 is configured to drive the reagent dispensing member 500 to move so that the reagent dispensing member 500 draws or discharges the reagent under the action of the reagent dispensing power device. The sample adding power device and the reagent dispensing power device may adopt all-purpose fluid quantitative devices such as syringe, plunger pump, and dosing pump.

The sample conveying unit 400 may include a sample rack 410, a sample tube 430, and a conveying track 420. The sample rack 410 may cooperate with the conveying track 420, the sample tube 430 is placed on the sample rack 410, and the sample tube 430 is configured to hold the sample, for example, about five to ten sample tubes 430 may be placed on each sample rack 410. When the sample rack 410 drives the sample tube 430 to move along the conveying track 420 to a designated position, the sample adding member 300 draws the sample in the sample tube 430, and dispenses the sample into the empty reactor 20.

The supply silo 130 is configured to store clean and empty reactors 20. The sorting mechanism may be configured to arrange the reactors 20 placed in disorder from the supply silo 130 so as to sort them in a certain order. The supply slide 140 introduces the sorted reactors 20 into the buffer unit 100 one by one, and the buffer unit 100 is configured to buffer the reactors 20 conveyed by the supply slide 140.

Referring to FIG. 1, in some embodiments, the whole liquid dispensing device 11 has a receiving position 33, a sample adding position 34, and a removing position 35. The buffer unit 100 includes a turntable 110. The turntable 110 can rotate around its own central axis. A plurality of buffer positions 101 are provided on the turntable 110, and the buffer positions 101 are configured to carry the reactors 20. The buffer positions 101 may be accommodating holes, and certainly, the accommodating holes may also be replaced by solid structures such as brackets, as long as the reactors 20 can be placed on the turntable 110. The buffer positions 101 are distributed at intervals along a circumferential direction of the turntable 110. When the turntable 110 rotates, it can drive the buffer positions 101 to move between the receiving position 33, the sample adding position 34, and the removing position 35, so that the reactor 20 on the turntable 110 moves between the receiving position 33, the sample adding position 34, and the removing position 35. Obviously, the turntable 110 drives the reactor 20 to make circular movement between the receiving position 33, the sample adding position 34, and the removing position 35.

Specifically, the reactor 20 from the supply slide 140 will enter the buffer position 101 on the turntable 110 at the receiving position 33. When the turntable 110 drives an empty reactor 20 to move to the sample adding position 34, the sample adding member 300 may draw the sample from the sample tube 430 so as to dispense the sample into the reactor 20. When the turntable 110 drives the reactor 20 already containing the sample to continue to move to the removing position 35, the transfer unit 700 will remove the reactor 20 already containing the sample from the turntable 110 at the removing position 35 and transfer the reactor to the ferrying unit 200.

The buffer positions 101 are arranged at intervals along the circumferential direction of the turntable 110. The buffer units 100 may only be arranged to form one buffer circle, which is provided close to an edge of the turntable 110. Certainly, the buffer positions 101 may also be arranged to form a plurality of buffer circles, and the plurality of buffer circles are concentrically arranged around the central axis of the turntable 110.

Figure 3:
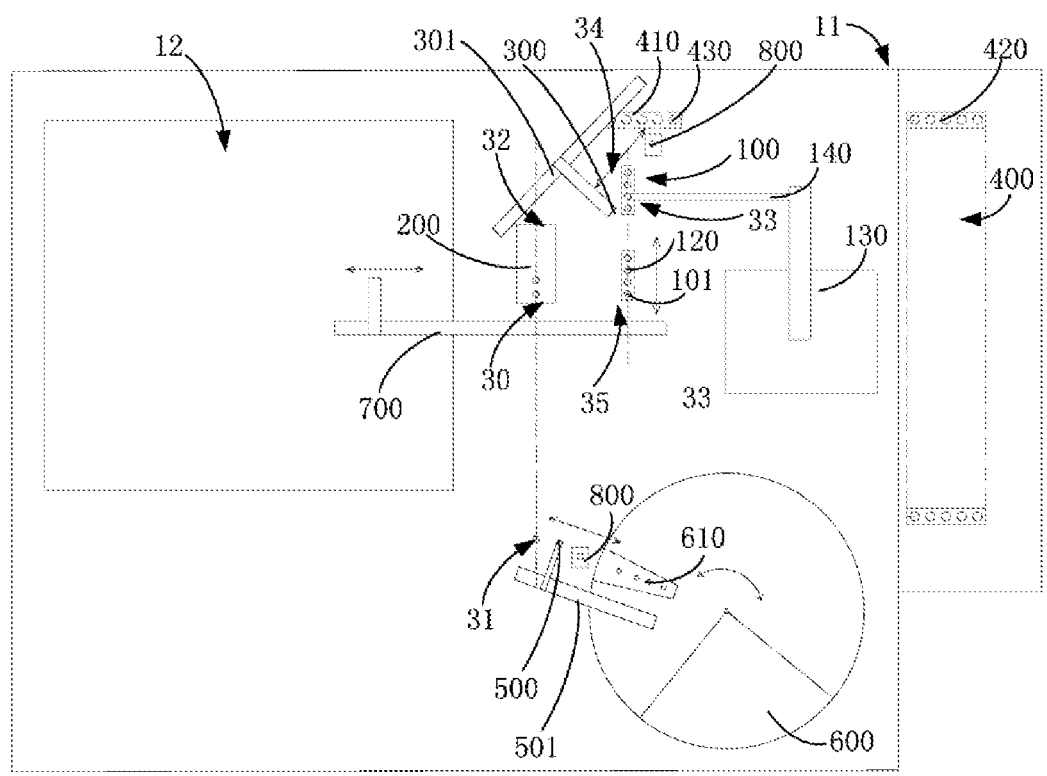
FIG. 3 is a plane structural schematic view of a second exemplary immunity analyzer provided in the first embodiment.

Referring to FIG. 3, in some embodiments, the buffer unit 100 includes a sliding block 120, the sliding block 120 is also provided with the buffer positions 101 for placing the reactor 20, and the buffer positions 101 on the sliding block 120 may also be accommodating holes. The buffer positions 101 may be only distributed at intervals along a straight line on the sliding block 120 to form a row. Certainly, the buffer positions 101 may be distributed at intervals on the sliding block 120 along a straight line to form multiple rows, in this case, the multiple rows of buffer positions 101 are distributed and arranged on the sliding block 120 in a matrix form. The sliding block 120 makes linear movement between the receiving position 33, the sample adding position 34, and the removing position 35, so as to drive the buffer positions 101 (corresponding to the reactors 20) thereon to move between the receiving position 33, the sample adding position 34, and the removing position 35. Similarly, referring to the above operation mode of the turntable 110, the reactor 20 enters the sliding block 120 at the receiving position 33, the sample adding member 300 dispenses the sample into the reactor 20 located at the sample adding position 34, and the transfer unit 700 will remove the reactor 20 already containing the sample from the sliding block 120 at the removing position 35 and transfer the reactor to the ferrying unit 200. In this embodiment, the sliding block 120 and the buffer positions 101 thereon reciprocate linearly between the receiving position 33, the sample adding position 34, and the removing position 35 to complete the receipt of the reactor 20, sample dispensing, and removal of the reactor 20 already containing the sample. The volume of the sliding block 120 itself may be designed to be smaller, meanwhile, an area of a region covered by a linear movement trajectory of the sliding block 120 is small, which is beneficial to optimized space layout of the supply silo 130, the supply slide 140, the sample conveying unit 400, the sample adding member 300, the transfer unit 700 and so on, can make the liquid dispensing device 11 more compact, and has a lower cost.

Figure 4:
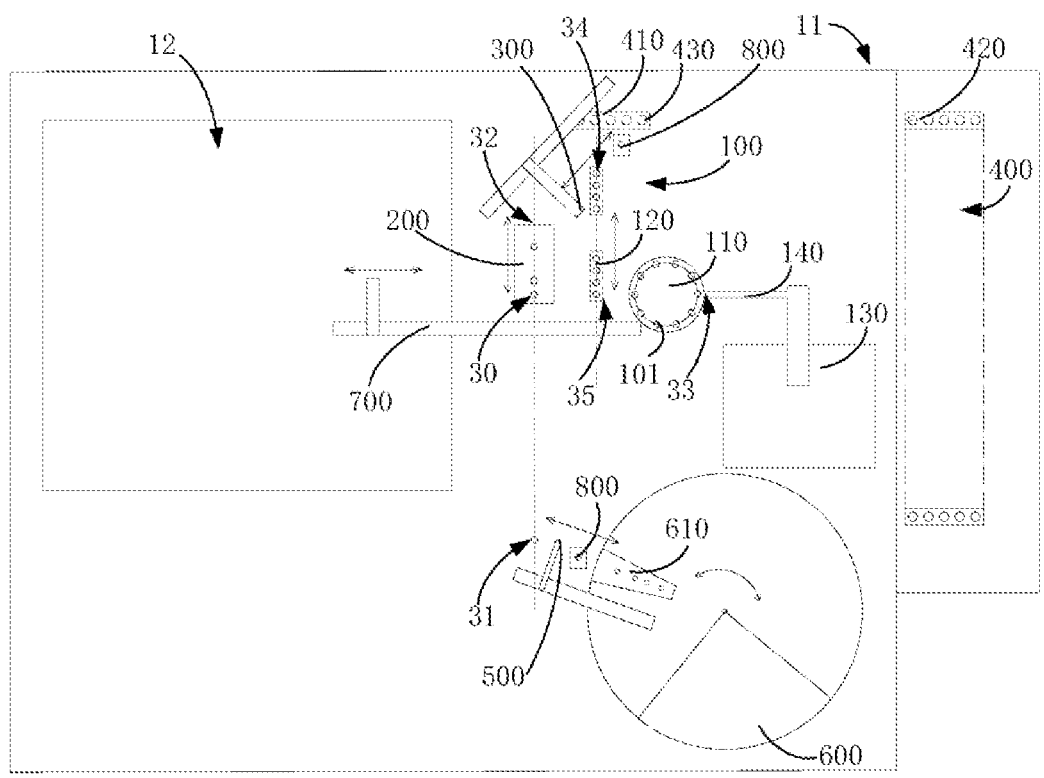
FIG. 4 is a plane structural schematic view of a third exemplary immunity analyzer provided in the first embodiment.

Referring to FIG. 4, in some embodiments, the buffer unit 100 includes both the turntable 110 and the sliding block 120 each provided with the buffer positions 101, the turntable 110 rotates around its own central axis, the turntable 110 can drive the buffer positions 101 thereon to pass through the receiving position 33, and the reactor 20 on the supply slide 140 will enter the buffer position 101 on the turntable 110 at the receiving position 33. The sliding block 120 makes linear movement between the sample adding position 34 and the removing position 35. When the turntable 110 drives the empty reactor 20 to rotate by a set angle from the receiving position 33, the transfer unit 700 may remove the empty reactor 20 from the turntable 110 and transfer the empty reactor to the sliding block 120 located at the removing position 35. When the sliding block 120 drives the reactor 20 to move to the sample adding position 34, the sample adding member 300 dispenses the sample into the empty reactor 20, subsequently, after the sliding block 120 drives the reactor 20 containing the sample to move to the removing position 35, the transfer unit 700 removes the reactor 20 containing the sample from the sliding block 120 at the removing position 35 and transfers the reactor to the ferrying unit 200.

Figure 2:
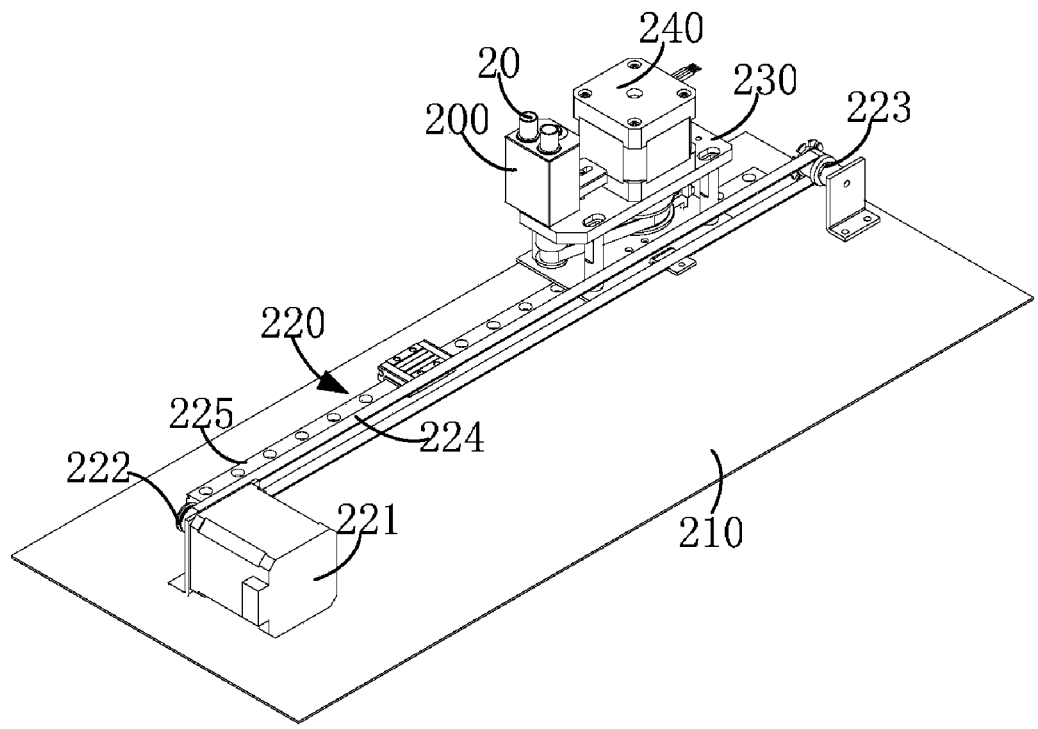
FIG. 2 is a partial perspective structural schematic view containing a ferrying unit in FIG. 1.

Referring to FIG. 2, in some embodiments, the liquid dispensing device 11 further includes a frame 210, a conveyor 220, a support 230, and a driver 240. The conveyor 220 is provided on the frame 210. The conveyor 220 is configured to drive the support 230 to slide relative to the frame 210. The conveyor 220 includes a motor 221, a driving wheel 222, a driven wheel 223, and a synchronous belt 224. The motor 221 is configured to drive the driving wheel 222 to rotate. The synchronous belt 224 is wound on the driving wheel 222 and the driven wheel 223, and when the motor 221 rotates, the driving wheel 222 and the driven wheel 223 drive the synchronous belt 224 to move. Certainly, in other embodiments, the conveyor 220 may also be replaced by one or several of transmission mechanisms such as screw rod mechanism, and gear-rack.

Specifically, the frame 210 may be provided with a sliding rail 225, the support 230 cooperates with the sliding rail 225, the synchronous belt 224 is connected to the support 230 and drives the support 230 to slide along an extending direction of the sliding rail 225, the driver 240 and the ferrying unit 200 are both provided on the support 230, the ferrying unit 200 is configured to place the reactor 20, and the driver 240 can drive the ferrying unit 200 to generate eccentric oscillation, so that the sample and the reagent (reactants) in the reactor 20 are uniformly mixed due to the generation of non-contact eccentric oscillation.

A plurality of receiving holes may be provided on the ferrying unit 200, and the reactors 20 are inserted into the receiving holes, so as to realize the bearing effect of the ferrying unit 200 on the reactors 20. Certainly, the receiving holes may also be replaced by solid structures such as brackets, as long as the reactors 20 can be placed on the ferrying unit 200.

In some embodiments, the whole liquid dispensing device 11 further has an initial position 30 and a first position 31, and when the motor 221 runs, the ferrying unit 200 can be enabled to make linear reciprocation between the initial position 30 and the first position 31. When the ferrying unit 200 is located at the initial position 30, the transfer unit 700 may transfer the reactor 20 containing the sample from the buffer unit 100 to the ferrying unit 200 located at the initial position 30. Then, the ferrying unit 200 drives the reactor 20 containing the sample to move to the first position 31, and the reagent dispensing member 500 will draw the reagent from the storage unit 600 for storing the reagent, and dispense the reagent into the reactor 20 located at the first position 31. Then, in the process of linear movement of the ferrying unit 200, the driver 240 may drive the ferrying unit 200 to generate eccentric oscillation, so as to uniformly mix the sample and the reagent in the reactor 20, in this way, the uniform mixing of the reactants and the movement of the ferrying unit 200 may be performed in parallel, that is, the ferrying unit 200 can uniformly mix the reactants in the reactor 20 while moving, thus improving the efficiency and effect of the uniform mixing, thereby increasing the test throughput of the whole device. Certainly, when the ferrying unit 200 is stationary before and after movement, the driver 240 may also drive the ferrying unit 200 to generate eccentric oscillation so as to uniformly mix the sample and the reagent in the reactor 20. The ferrying unit 200 returns the reactor 20 having been dispensed with the reagent to the initial position 30, and the transfer unit 700 may remove the reactor 20, in which the reactants have been uniformly mixed, from the ferrying unit 200 at the initial position 30, and transfer the reactor to the reaction device 12, so that the reactor 20 performs incubation, bound-free, and measurement treatments on the reaction device 12.

It can thus be seen that the driver 240 directly generates eccentric oscillation for the ferrying unit 200, so that the reactants in the reactor 20 on the ferrying unit 200 are uniformly mixed, without an additional separate mixing device, the linear movement or stationary state of the ferrying unit 200 does not limit the uniform mixing of the reactants in the reactor 20, then the problems such as complexity, low mixing efficiency, and poor mixing effect of the prior mixing device are solved. In addition, the ferrying unit 200 makes linear movement between the sample adding member 300, the transfer unit 700, and the reagent dispensing member 500. On one hand, the control difficulty of the linear movement is reduced, so that the ferrying unit 200 moves more accurately and efficiently, the ferrying unit 200 is prevented from deviating from a specified stop position, the ferrying unit 200 can be ensured to be accurately and timely stopped at the initial position 30 or the first position 31, the reactor 20 containing the sample can be ensured to be smoothly transferred to the ferrying unit 200 at the initial position 30, and the reagent dispensing member 500 can also be ensured to reliably add the reagent into the reactor 20 at the first position 31; on the other hand, the reactor 20 containing the sample is carried on the buffer unit 100 so as to wait to be transferred to the ferrying unit 200 and added with the reagent, which is then mixed uniformly, without the need of transferring all the reactors 20 containing the sample to the ferrying unit 200, thus, the bearing space of the buffer unit 100 is fully utilized, so that the number of reactors 20 simultaneously carried by the ferrying unit 200 is reduced, ensuring the volume of the ferrying unit 200 to be designed smaller, and the structure to be more compact; meanwhile, an area of a region covered by the linear movement trajectory of the ferrying unit 200 is small, which overcomes the limitation that the sample adding member 300, the transfer unit 700, and the reagent dispensing member 500 in the prior art must be arranged along a large-radius rotation or rotary disk, optimizes the space layout and the control flow of components or units, can more efficiently connect and coordinate logic actions among the sample adding member 300, the transfer unit 700, and the reagent dispensing member 500, which not only enables the immunity analyzer to be more compact, but also improves the overall operation efficiency.

By dispensing the sample into the reactor 20 on the buffer unit 100, transferring the reactor 20 having been dispensed with the sample to the ferrying unit 200 to be dispensed with the reagent and uniformly mixing the resultant, the dispensing of the sample and the dispensing of the reagent are realized on different separate units, respectively, and the uniform mixing is directly realized on the ferrying unit, so that the problem that the dispensing of the sample and the dispensing of the reagent are mutually restricted and the problem that the reactants are uniformly mixed separately at a specific position in the prior art are solved, thus improving the efficiency of liquid dispensing and uniform mixing.

In some embodiments, the storage unit 600 is a rotatable disk, the storage unit 600 is provided close to the first position 31, a plurality of storage portions 610 are provided on the storage unit 600, the storage portions 610 are configured to place and store a reagent container, the reagent is stored in the reagent container, and the reagent dispensing member 500 is configured to draw the reagent components in the reagent container on the storage portion 610, and dispense the reagent components into the reactor 20 located at the first position 31. The number of storage portions 610 may be set according to needs, and the number of storage portions 610 on each storage unit 600 is preferably 15-50 taking use requirements, cost, and layout into consideration, for example, the number of storage portions 610 on each storage unit 600 is 25, in this way, two storage units 600 may store 50 reagent containers in total on line simultaneously. Each storage unit 600 stores all the reagent components required for corresponding analytical item, for example, in one analytical item, three reagent components, i.e. magnetic particle, marker, and dissociating agent, have to be dispensed into the reactor 20, then the three components, i.e. the magnetic particle, marker, and dissociating agent, are placed on the same storage unit 600. When a certain analytical item needs to be loaded with a plurality of reagent containers so as to expand a test amount of the item on a machine, the plurality of reagent containers may be stored in each storage unit 600 in any suitable combination. For example, when the number of storage units 600 is two, three TSH (thyroid stimulating hormone) reagent containers each containing 100 tests need to be loaded, and three TSH reagent containers may be all loaded in the same storage unit 600, or one TSH reagent container may be loaded in one of the storage units 600, and the other two TSH reagent containers are loaded in another storage unit 600. When the storage unit 600 rotates intermittently, the storage portion 610 may be driven to move to a designated liquid-drawing position, so that the reagent dispensing member 500 draws the reagent on the storage portion 610 at the liquid-drawing position and dispenses the reagent into the reactor 20.

In the process of rotation (revolution) of the storage portions 610 with the storage unit 600, at least one cavity (such as a magnetic particle cavity holding the magnetic particle reagent components) of the reagent container on the storage portion 610 spins around its own central axis, so that the magnetic particle reagent components existing in a form of solid suspension generate vortex, thereby avoiding precipitation of solid matters (such as magnetic particles) therein. The storage unit 600 may be further provided with a scanner, and the scanner may identify bar code information of the reagent container on the storage portion 610, so as to distinguish different reagents. The storage unit 600 may further be provided with a refrigerator, and the refrigerator may perform refrigeration processing for the reagent in the storage portion 610, so as to realize long-term on-line storage of the reagent.

The transfer unit 700 is configured to transfer the reactor 20 between the ferrying unit 200, the buffer unit 100, and the reaction device 12, and the transfer unit 700 may make horizontal movement and vertical movement. Obviously, the removing position 35 and the initial position 30 are both located on the movement trajectory of the transfer unit 700.

Figure 9:
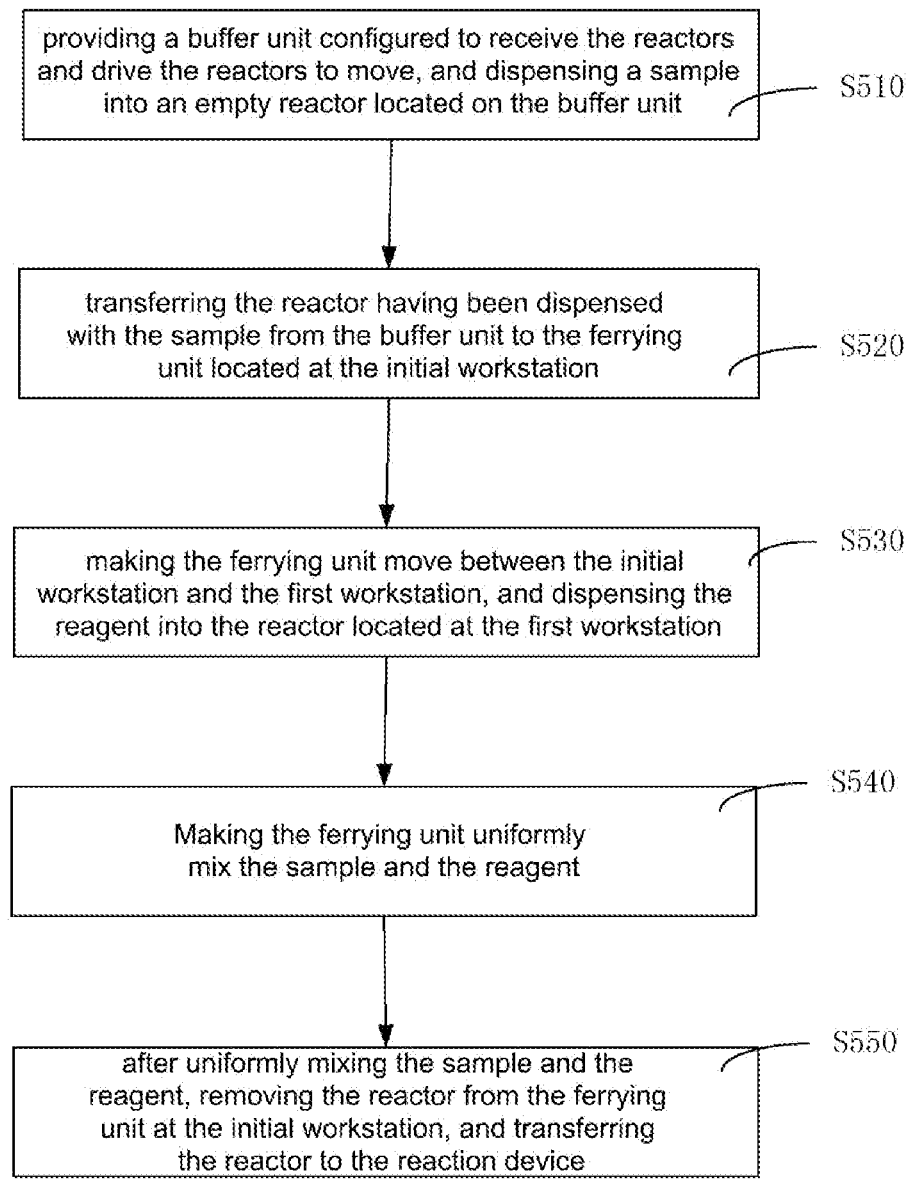
FIG. 9 is a block flowchart of a first liquid dispensing method.

When the liquid dispensing device 11 is adopted to dispense the sample and the reagent into the reactor 20, and uniformly mix the sample and the reagent, a first liquid dispensing method may be formed, wherein the first liquid dispensing method is mainly characterized in that the sample is dispensed from the buffer unit 100 (not from the ferrying unit 200) into the reactor 20. Referring to FIG. 9, the first liquid dispensing method mainly includes the following steps.

S510, providing a buffer unit 100 configured to receive the reactors 20 and drive the reactors 20 to move, and dispensing a sample into an empty reactor 20 located on the buffer unit 100.

S520, making the ferrying unit 200 stop at the initial position 30, and transferring the reactor 20 having been dispensed with the sample from the buffer unit 100 to the ferrying unit 200 located at the initial position 30.

S530, making the ferrying unit 200 move between the initial position 30 and the first position 31, and dispensing the reagent into the reactor 20 located at the first position 31, wherein certainly, the ferrying unit 200 may be enabled to make linear movement between the initial position 30 and the first position 31, and wherein the sample can be dispensed into the empty reactor 20 on the buffer unit 100 while the ferrying unit 200 carrying the reactor 20 having been dispensed with the sample is moving or stationary.

S540, making the ferrying unit 200 uniformly mix the sample and the reagent after the reagent is dispensed into the reactor 20, wherein the ferrying unit 200 may uniformly mix the reactants in the reactor 20 in a manner of non-contact eccentric oscillation, thereby eliminating carryover contamination of other contact-type stirring on the reactants, and in order to increase the test throughput, the ferrying unit 200 may be enabled to uniformly mix the sample and the reagent in the reactor 20 during movement from the first position 31 to the initial position 30.

S550, making the ferrying unit 200 stop at the initial position 30, and after uniformly mixing the sample and the reagent, by the transfer unit 700, removing the reactor 20 from the ferrying unit 200 at the initial position 30, and transferring the reactor to the reaction device 12.

In the first liquid dispensing method, a shortest time window, in which a sequence of actions in the above steps S520, S530, S540, and S550 executed by the ferrying unit 200 can be cyclically reproduced, is recorded as operation period T, and the ferrying unit 200 is allowed to, within one operation period T, receive the reactor 20 having been dispensed with the sample at the initial position 30, linearly move to the first position 31 to undergo dispensing of the reagent into the reactor 20, uniformly mix the reactants in the reactor 20, and linearly move to the initial position 30 to make the reactor 20 leave.

A time interval between continuously dispensing the sample into at least two empty reactors 20 located on the buffer unit 100 is recorded as a sample dispensing interval t, wherein t=T or there is at least one t, and t<T. When t=T, in the interval of each operation period T, the sample is dispensed once into the empty reactor 20 located on the buffer unit 100. In particular, when t<T, in the interval of the operation period T, the sample is dispensed more than once into the empty reactor 20 located on the buffer unit 100. When there is at least one t, and t<T, the time for dispensing the sample into the empty reactor 20 located on the buffer unit 100 is not fixed, and may not be limited by the operation period T, and the interval of dispensing the sample is determined according to the needs of test, making the test more flexible and more efficient.

In the first liquid dispensing method, the sample is dispensed only from the buffer unit 100 into the reactor 20, but not from the ferrying unit 200 into the reactor 20, in this way, the time for dispensing the sample from the ferrying unit 200 into the reactor 20 can be saved, thus improving the operation efficiency of the liquid dispensing device. In some embodiments, when the buffer unit 100 only includes the turntable 110 making circular movement or only includes the sliding block 120 making linear movement, the step of dispensing the sample into the buffer unit 100 includes the following sub-steps:

inputting the reactor 20 from the receiving position 33 to the buffer unit 100;

making the reactor 20 move with the buffer unit 100 from the receiving position 33 to the sample adding position 34, and dispensing the sample into the reactor 20 located at the sample adding position 34; and making the reactor 20 move with the buffer unit 100 from the sample adding position 34 to the removing position 35, wherein the reactor 20 can be transferred from the removing position 35 to the ferrying unit 200.

In some embodiments, when the buffer unit 100 includes both the turntable 110 making the circular movement and the sliding block 120 making the linear movement, the step of dispensing the sample into the buffer unit 100 includes the following sub-steps:

inputting the reactor 20 from the receiving position 33 onto the turntable 110 of the buffer unit 100;

making the turntable 110 move around its own central axis, wherein the reactor 20 rotates by a set angle with the turntable 110;

transferring the reactor 20 from the turntable 110 to the sliding block 120 of the buffer unit 100, wherein the reactor 20 makes linear movement with the sliding block 120 to the sample adding position 34, and dispensing the sample into the reactor 20 located at the sample adding position 34; and making the reactor 20 make linear movement with the sliding block 120 from the sample adding position 34 to the removing position 35, wherein the reactor 20 can be transferred from the removing position 35 to the ferrying unit 200.

In order to ensure the maximum test throughput, one reactor 20 in which the reactants have been uniformly mixed must be removed from the ferrying unit 200 within a specified period of time. Thus, the shorter the time from a single reactor 20 entering the ferrying unit 200 to leaving the ferrying unit 200 (i.e., total retention time of the single reactor 20 on the ferrying unit 200) is, the greater the test throughput is. In the conventional solution of dispensing both the sample and the reagent from the ferrying unit 200 into the reactor 20, since the sample and the reagent are dispensed both from the ferrying unit 200 to the reactor 20 thereon, the retention time (duration) of the reactor 20 on the ferrying unit 200 will at least include sample dispensing time, reagent dispensing time, moving time of the ferrying unit 200, and time of uniformly mixing the reactants.

However, for the first liquid dispensing method, the sample is dispensed only from the buffer unit 100 into the reactor 20 (the sample is not dispensed from the ferrying unit 200 into the reactor 20), that is, the sample is dispensed only into the reactor 20 located at the buffer unit 100; after the reactor 20 containing the sample is transferred from the buffer unit 100 to the ferrying unit 200, the reagent will be dispensed into the reactor 20 already containing the sample located on the ferrying unit 200. Therefore, compared with the conventional solution, on the basis that the operation efficiencies of both the sample adding member 300 and the reagent dispensing member 500 are the same, and the running speed of the ferrying unit 200 is the same, the retention time of the reactor 20 on the ferrying unit 200 only includes the reagent dispensing time, moving time of the ferrying unit 200, and the time of uniformly mixing the reactants, thus, the sample dispensing time is saved, and the reactor 20 stays on the ferrying unit 200 for a shorter time, so that the reactor 20 can uniformly mix the reactants in a relatively short period of time and leave the ferrying unit 200, thus increasing the test throughput of the whole immunity analyzer 10.

In fact, for the first liquid dispensing method, the dispensing of the sample will not be restricted by a moving speed of the ferrying unit 200 or a position where the ferrying unit is located. When the ferrying unit 200 carrying the reactor 20 having been dispensed with the sample is moving or stationary, the sample adding member 300 may fully utilize the idle waiting time, so as to dispense the sample in advance from the buffer unit 100 into the reactor 20, then the total retention time of a single reactor 20 on the ferrying unit 200 is reduced, and finally the objective of increasing the maximum test throughput is achieved. Therefore, even when the reagent dispensing member 500 dispenses the reagent from the ferrying unit 200 into the reactor 20 thereon, the sample adding member 300 may dispense the sample from the buffer unit 100 into the reactor 20 thereon, that is, the sample and the reagent may be dispensed synchronously, thereby eliminating the time for dispensing the sample on the ferrying unit 200. For the conventional solution, the dispensing of the sample cannot get rid of restrictions of the moving speed of the ferrying unit 200 or a position where the ferrying unit is located, and only when the ferrying unit 200 reaches the initial position 30, the sample adding member 300 can dispense the sample from the ferrying unit into the reactor 20, then it is impossible to dispense the sample and the reagent into the reactor 20 at the same moment.

Certainly, on the basis of ensuring the same test throughput as the conventional solution, for the first liquid dispensing method, the running speeds (operation efficiencies or operation loads) of the ferrying unit 200, the sample adding member 300, and the reagent dispensing member 500 further may be suitably decreased, so as to reduce the difficulty in controlling the movement of the ferrying unit 200, the sample adding member 300, and the reagent dispensing member 500, and vibrations, noises, and failures caused by high-speed operation of various components in the liquid dispensing device 11 are also reduced, thus improving the stability and reliability of the operation of the whole liquid dispensing device 11.

Figure 10:
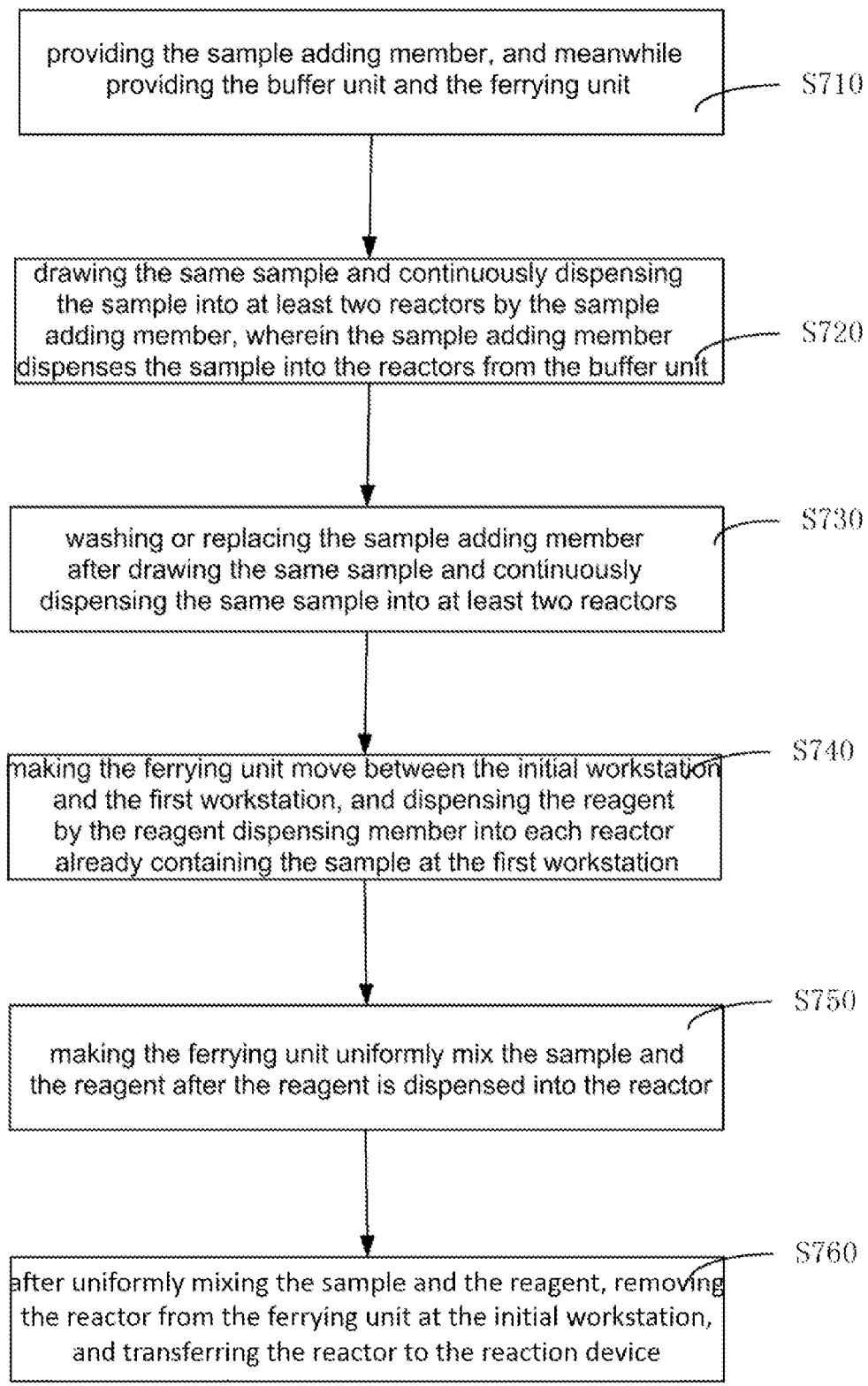
FIG. 10 is a block flowchart of a second liquid dispensing method.

When the above liquid dispensing device 11 is adopted to dispense the sample and the reagent into the reactor 20, and uniformly mix the sample and the reagent, a second liquid dispensing method also may be formed, wherein the second liquid dispensing method is mainly characterized in that the same sample is drawn by the sample adding member 300 and dispensed in multiple times into at least two reactors 20; meanwhile, after the same sample is drawn and continuously dispensed into at least two reactors, the sample adding member 300 is washed or replaced, and in the process of drawing the same sample and continuously dispensing the same sample into at least two reactors, the sample adding member 300 is not washed or replaced. Referring to FIG. 10, the second liquid dispensing method mainly includes the following steps.

S710, providing the sample adding member 300, and meanwhile providing the buffer unit 100 and the ferrying unit 200.

S720, drawing the same sample and continuously dispensing the sample into at least two reactors 20 of the buffer unit 100 by the sample adding member 300, wherein a time interval between continuously dispensing the sample into at least two empty reactors 20 located on the buffer unit 100 is recorded as a sample dispensing interval t, wherein it could be understood by a person skilled in the art that the same sample herein specifically refers to the same sample to be tested (that is, corresponding to a certain subject, such as a certain patient's sample) that needs to be detected at least twice, and the at least two times of detection may be for at least two different analytical items, and may also be at least two times of detection repeated for the same analytical item; and different samples refer to samples of different subjects.

S730, washing or replacing the sample adding member 300 after drawing the same sample and continuously dispensing the same sample into at least two reactors, wherein in the process of drawing the same sample and continuously dispensing the same sample into at least two reactors, the sample adding member 300 is not washed or replaced, in particular, the sample adding member 300 is washed or replaced between dispensing of different samples.

S740, recording a shortest time window, in which a sequence of actions executed by the ferrying unit 200 can be cyclically reproduced, as operation period T, making the ferrying unit 200 move between the initial position 30 and the first position 31, and dispensing the reagent by the reagent dispensing member 500 into each reactor 20 already containing the sample at the first position 31, wherein specifically, the reagent is dispensed by the reagent dispensing member 500 at the first position 31 into each reactor 20 already containing the sample on the ferrying unit 200. Similar to the ferrying unit 200, the reagent dispensing member 500 also dispenses the reagent according to the operation period T, i.e. dispenses the reagent into only one reactor 20 already containing the sample within each operation period T. Therefore, for at least two reactors, after the sample is dispensed by the sample adding member 300 according to the sample dispensing interval t, the interval time for dispensing the reagent by the same reagent dispensing member 500 is at least T.

S750, making the ferrying unit 200 uniformly mix the sample and the reagent after the reagent is dispensed into the reactor 20, wherein the ferrying unit 200 may uniformly mix the reactants in the reactor 20 in a manner of non-contact eccentric oscillation, thereby eliminating carryover contamination of other contact-type stirring on the reactants. In order to increase the test throughput, the ferrying unit 200 may be enabled to uniformly mix the sample and the reagent in the reactor 20 during movement from the first position 31 to the initial position 30.

S760, after uniformly mixing the sample and the reagent, by the transfer unit 700, removing the reactor 20 from the ferrying unit 200 at the initial position 30, and transferring the reactor to the reaction device 12.

For other similarities of the second liquid dispensing method, reference may be made to the first liquid dispensing method above, and details are not described herein again.

In some embodiments, the sample adding member 300 adopts an elongated cylindrical sample needle, and after drawing the same sample and continuously dispensing the same sample into at least two reactors, in particular, between the dispensing of different samples, the sample needle is moved to the washing tank 800, to wash an inner wall and an outer wall of the sample needle simultaneously, so as to eliminate carryover contamination between different samples. During the washing, a washing liquid is injected into an inner cavity of the sample needle through a hydrodynamic device such as a syringe or a pump, then the washing liquid flowing through the inner cavity of the sample needle at a certain flow speed will flush the inner wall of the sample needle so as to achieve the washing effect, meanwhile, the outer wall of the sample needle is sprayed with or immersed in the washing liquid to wash the outer wall of the sample needle, and the washing liquid flowing out from the inner cavity and the outer wall of the sample needle may be simultaneously discharged into the washing tank 800. In order to ensure thorough washing of the inner wall and the outer wall of the sample needle so as to eliminate the carryover contamination, and meanwhile ensure the operation efficiency of the sample needle and the test throughput of the immunity analyzer 10, the duration for washing the sample needle is 2 seconds to 10 seconds.

In some embodiments, the sample adding member 300 adopts a disposable nozzle, and the disposable nozzle is replaced after the same sample is drawn and continuously dispensed into at least two reactors 20. In particular, between the dispensing of different samples, the disposable nozzle is replaced. In this way, the washing of the disposable nozzle can be omitted, the washing time is reduced so as to improve the efficiency, and meanwhile, the cost of the disposable nozzle can be compensated by reducing the cost of the washing liquid.

Figure 6:
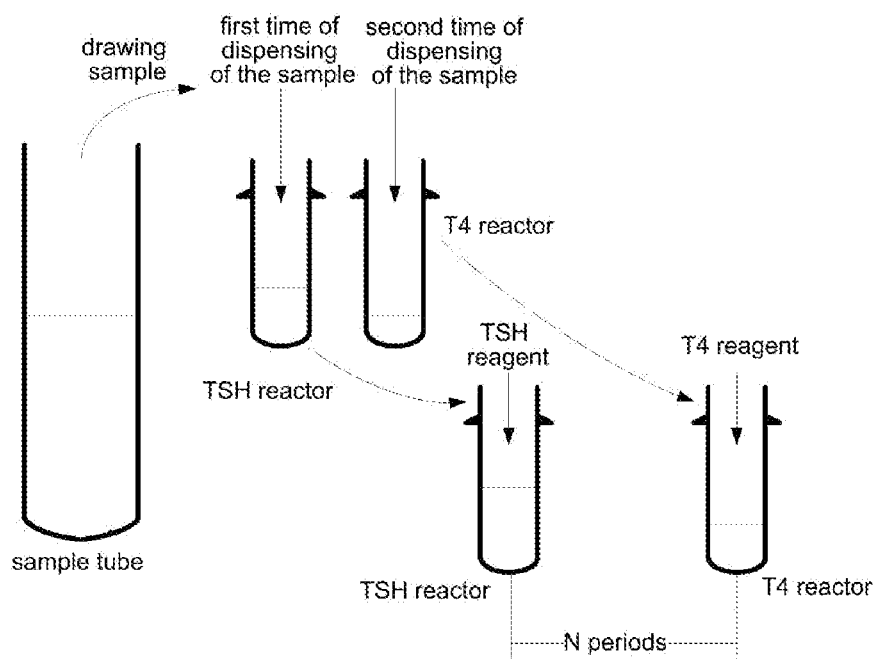
FIG. 6 is a schematic diagram of continuously dispensing the same sample into at least two reactors.
Figure 7:
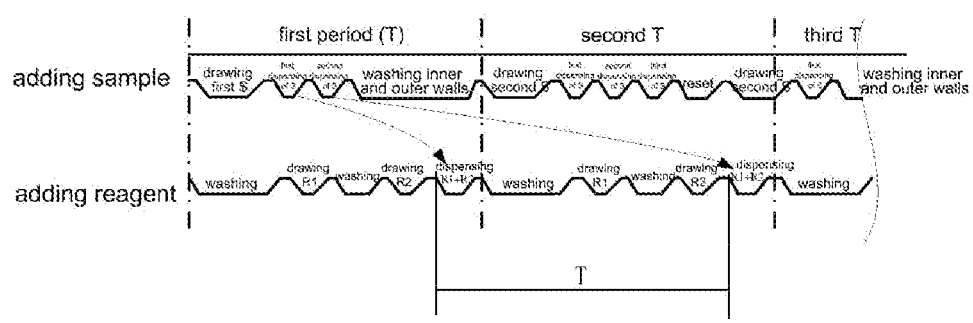
FIG. 7 is a timing diagram of dispensing a sample and a reagent into a reactor.

Referring to FIG. 6 and FIG. 7 together, in some embodiments, when a sum of samples required for all analytical items corresponding to the samples to be tested does not exceed a capacity of the sample needle, that is, when the capacity of the sample adding member 300 is greater than a total amount of the same sample required for various reactors 20, the sample adding member 300 draws the same sample only once and continuously dispenses the same sample into different reactors 20 in multiple times. For example, the sample adding member 300 needs to draw a same blood sample (denoted as first S) to detect two items in the five items of thyroid function, i.e. TSH item and T4 item, wherein for the reactor 20 for detecting the TSH item, the reactor 20 (denoted as TSH reactor) needs 100 microliters of blood sample; and for the reactor 20 for detecting the T4 item, the reactor 20 (denoted as T4 reactor) requires 50 microliters of blood sample. In this case, the capacity of the sample adding member 300 is greater than 150 microliters, that is, the capacity of the sample adding member 300 is greater than a sum of the capacity of the blood sample required by the TSH reactor and the blood sample required by the T4 reactor, therefore, the sample adding member 300 draws at least 150 microliters of blood sample (first S) from the sample tube 430 at one time, and when dispensing the blood sample, the buffer unit 100 drives the TSH reactor to move to the sample adding position 34, the sample adding member 300 dispenses 100 microliters of blood sample (first S) into the TSH reactor; then, the buffer unit 100 continues to drive the T4 reactor to move to the sample adding position 34, and after the sample dispensing interval t (there is at least one t, and t<T), the sample adding member 300 dispenses 50 microliters of blood sample (first S) into the T4 reactor. Between the dispensing of the blood sample into the TSH reactor and the T4 reactor, as the blood sample is the same, the sample adding member 300 does not need to be washed. Certainly, the sample adding member 300 may be moved to above the washing tank 800 or in the washing tank 800 for hysteresis error calibration, and may also stay at the sample adding position 34. The reagent dispensing member 500 subsequently dispenses the TSH reagent into the TSH reactor, wherein the TSH reagent may include an R1 component and an R2 component, and after at least one operation period T, dispenses the T4 reagent into the T4 reactor, wherein the T4 reagent may also include the R1 component and the R2 component.

In some embodiments, when a sum of samples required for all analytical items corresponding to the samples to be tested exceeds the capacity of the sample needle, i.e., when the capacity of the sample adding member 300 is less than the total amount of the same sample required for various reactors 20, the sample adding member 300 draws the same sample (denoted as second S) in multiple times and dispenses the same sample into different reactors 20 at the sample dispensing interval t (there is at least one t, and t<T). For example, the same sample (second S) needs to be dispensed into four reactors 20 so as to detect four different items. Provided that the sample adding member 300 has a capacity of 500 microliters, and the total amount of the same sample required for the four reactors 20 exceeds 500 microliters, in this case, the sample adding member 300 may draw the same sample in two times so as to dispense the same sample (second S) into the four reactors 20. In operation, the sample adding member 300 draws less than 500 microliters of the sample (second S) for the first time, and continuously dispenses the sample into three reactors 20 in a set amount in three times, and then the sample adding member 300 draws less than 500 microliters of the sample for the second time, and dispenses the sample into the last reactor 20 in a set amount. Between the drawing of the same sample (second S) in the first time and in the second time by the sample adding member 300, the sample adding member 300 is run into the washing tank 800 to reset the sample adding power device. Since the reset needs to be performed in the process of washing the sample adding member 300, and there is no problem of carryover contamination for the same sample, the sample adding member 300 only needs to be washed for a short period of time, so that the sample adding member 300 is ready for better completing the second time of sample drawing.

In some embodiments, for the sample dispensing interval t, there is at least one t, and t<T, i.e., there is at least one interval of operation period T, in which the operation efficiency of the sample adding member 300 is greater than that of the reagent dispensing member 500. For the same reactor 20 having been dispensed with the sample, the reagent dispensing member 500 can draw different reagent components and dispense the same into the reactor 20 in multiple times in each operation period T. Within the time interval of an operation period T in which the reagent dispensing member 500 dispenses each desired reagent component into a single reactor 20, the sample adding member 300 can dispense the sample into at least two reactors 20. In short, each reagent dispensing member 500 can dispense each reagent component into only one reactor 20 within a time interval of the operation period T, while the sample adding member 300 can dispense the sample into at least two reactors 20. Between the drawing of different reagent components by the reagent dispensing member 500, the reagent dispensing member 500 is washed so as to prevent carryover contamination of different reagent components; for example, different reagent components include the R1 component and the R2 component, the reagent dispensing member 500 successively draws the R1 component and the R2 component into the same reactor 20, and before the reagent dispensing member 500 draws the R2 component, the reagent dispensing member 500 that has just drawn the R1 component is washed so as to prevent carryover contamination of the R1 component to the R2 component.

Depending on the needs of the actual situation, the sample quantity each time drawn by the sample adding member 300 can be set to 10 microliters to 500 microliters, and the sample quantity required by each reactor 20 is 5 microliters to 250 microliters.

For the conventional solution, after the sample adding member 300 dispenses the sample into each reactor 20, the sample adding member 300 needs to be washed, so as to eliminate the carryover contamination caused by extending the sample adding member 300 into the sample tube 430 to draw the sample again and dispensing the sample, in this way, the number of washing times is increased, thereby causing at least the following three defects. First, a lot of time is consumed, which also reduces the operation efficiency of the sample adding member 300, thereby affecting the test throughput of the whole immunity analyzer 10. Secondly, a large amount of washing liquid is consumed, thus increasing the test cost of the immunity analyzer 10. Thirdly, due to more washing times, in order to ensure the operation efficiency of the sample adding member 300 and ensure the test throughput, the washing duration of the sample adding member 300 will be reduced, so that the sample adding member 300 cannot be washed thoroughly, and then the carryover contamination cannot be effectively eliminated.

The second liquid dispensing method has at least the following beneficial effects. Firstly, as the sample adding member 300 draws the same sample and continuously dispenses the same sample into at least two reactors 20, in the continuous dispensing of the same sample into the two reactors 20, the sample adding member 300 does not need to extend into the sample tube 430 again to draw the sample, nor the sample adding member 300 needs to be washed, therefore, the sample adding member 300 needs to be washed once at least every two reactors 20, then the phenomenon that the sample adding member 300 needs to be washed every other reactor 20 in the conventional solution is effectively avoided. This can reduce the number of washing times of the sample adding member 300, thereby improving the operation efficiency of the sample adding member 300 and the test throughput of the immunity analyzer 10. Secondly, when the sample adding member 300 is extended into the sample tube 430 multiple times to draw the same sample, the sample adding member 300 only needs to be washed for a short period of time, in this way, the sample adding member 300 can be made to collectively dispense a certain kind of same sample, and then collectively dispense another kind of same sample, thus reducing the switching frequency between different samples, and further functioning to reduce the washing times and the washing duration of the sample adding member 300. Thirdly, as the washing times of the sample adding member 300 are reduced, on the basis of guaranteeing the operation efficiency and the test throughput, the duration of washing the sample adding member 300 may be suitably prolonged each time, so as to thoroughly wash the sample adding member 300, and effectively reduce the risk of carryover contamination between different samples. Obviously, the reduction in washing times also will reduce the consumption of the washing liquid, which can reduce the test cost of the immunity analyzer 10. Fourthly, on the basis of improving the sample adding efficiency and effectively reducing the carryover contamination between the samples, the ferrying unit 200 and the reagent dispensing member 500 are enabled to efficiently coordinate and move, further improving the efficiency of reagent dispensing and reactant uniform mixing. In an operation period T, the reagent is dispensed by the reagent dispensing member 500 into each reactor 20 already containing the sample at the first position 31, the sample and the reagent are uniformly mixed by the ferrying unit 200, the sample dispensing is completed by the buffer unit, and the reagent dispensing and the reactant uniform mixing are completed on the ferrying unit, so that the efficiency of sample and reagent dispensing and reactant uniform mixing is improved, and thus the test efficiency and throughput of the immunity analyzer are improved, for example, the test throughput of the immunity analyzer of the present disclosure can break through the highest level (600 tests per hour) currently reported in the industry, and 720, 800 tests per hour or even higher test throughput can be achieved.

Figure 8:
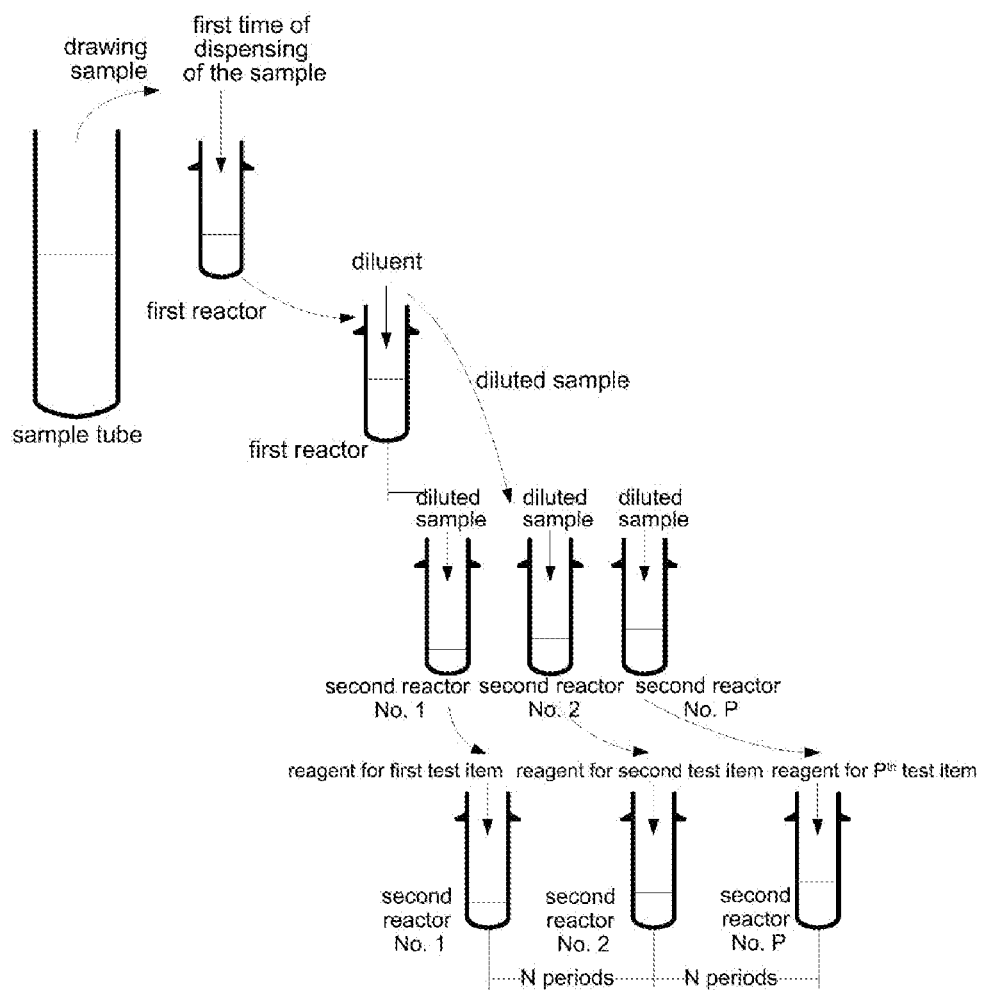
FIG. 8 is a schematic diagram of providing a diluted sample to at least two reactors.
Figure 11:
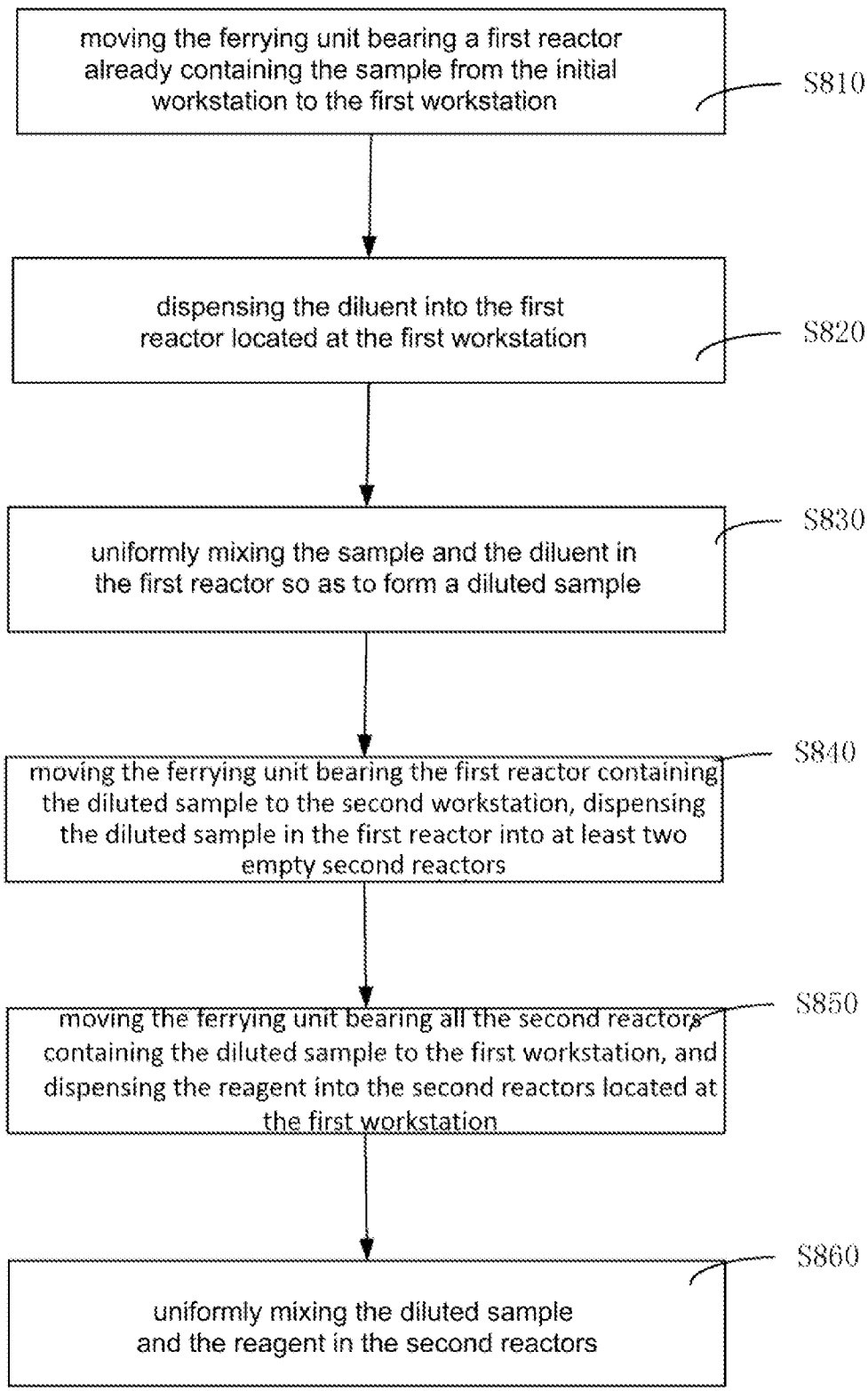
FIG. 11 is a block flowchart of a sample dilution method.

When the above liquid dispensing device 11 is adopted to dispense the sample and the diluent (the diluent may be regarded as a component of a reagent corresponding to an analytical item, as described above) into the reactor 20, uniformly mix the sample and the diluent to form a diluted sample, then dispense the diluted sample into a plurality of reactors 20, and finally dispense the reagent into the reactor 20 containing the diluted sample and uniformly mix the resultant, a sample dilution method can be formed. Referring to FIG. 8 and FIG. 11 together, the sample dilution method mainly includes the following steps:

S810, moving the ferrying unit 200 bearing a first reactor already containing the sample from the initial position 30 to the first position 31;

S820, dispensing the diluent into the first reactor located at the first position 31;

S830, uniformly mixing the sample and the diluent in the first reactor so as to form a diluted sample;

S840, moving the ferrying unit 200 bearing the first reactor containing the diluted sample to the second position 32, dispensing the diluted sample in the first reactor located at the second position into at least two empty second reactors, wherein certainly, the quantity of diluted sample dispensed into each empty second reactor may be different according to different analytical items, for example, the quantity of diluted sample dispensed into one of the second reactors may be greater than that dispensed into another second reactor;

S850, moving the ferrying unit 200 bearing the second reactors containing the diluted sample to the first position 31, and dispensing the reagent into the second reactors located at the first position 31; and S860, uniformly mixing the diluted sample and the reagent in the second reactors.

In some embodiments, referring to the relevant introduction in the first liquid dispensing method above, the first reactor is placed on the buffer unit 100, and after dispensing the sample into the first reactor on the buffer unit 100 by the sample adding member 300, the first reactor containing the sample is transferred from the buffer unit 100 to the ferrying unit 200 at the initial position 30. In other words, the sample is dispensed into the reactor 20 only from the buffer unit 100 (not from the ferrying unit 200), so that the dispensing of the sample is not restricted by the moving speed of the ferrying unit 200 or a position where the ferrying unit is located. When the ferrying unit 200 carrying the reactor 20 is moving or stationary, the sample can be dispensed from the buffer unit 100 (not from the ferrying unit 200) into the reactor 20, thus, the test throughput of the immunity analyzer 10 is improved.

In some embodiments, the empty second reactor is placed on the buffer unit 100, and after the diluted sample is dispensed into the second reactor, the second reactor containing the diluted sample is transferred from the buffer unit 100 to the ferrying unit 200 at the initial position 30. For the sample and the diluent in the first reactor and the diluent sample and the reagent in the second reactor, they are all uniformly mixed by the ferrying unit 200 itself, and the uniform mixing is carried out in a manner of non-contact eccentric oscillation. Meanwhile, the initial position 30 is provided between the first position 31 and the second position 32, and the ferrying unit 200 is enabled to make linear reciprocation between the initial position 30, the first position 31, and the second position 32.

In some embodiments, the buffer unit 100 is enabled to move between the receiving position 33, the sample adding position 34, and the removing position 35. The first reactor and the second reactor both enter the buffer unit 100 from the receiving position 33, the sample is dispensed from the sample adding position 34 into the first reactor, the diluted sample is also dispensed from the sample adding position 34 into the second reactor, and both the first reactor and the second reactor leave the buffer unit 100 at the removing position 35 and are transferred to the ferrying unit 200. When the buffer unit 100 is the turntable 110, the turntable 110 drives the first and second reactors to perform circular movement between the receiving position 33, the sample adding position 34, and the removing position 35. When the buffer unit 100 is the sliding block 120, the sliding block 120 drives the first and second reactors to make linear movement between the receiving position 33, the sample adding position 34, and the removing position 35.

For the conventional sample dilution method, the diluted sample each time formed from the uniform mixing by the liquid dispensing device 11 can only be used by one reactor 20, that is, the liquid dispensing device 11 should perform a separate uniform mixing process once for each reactor 20 so as to form the diluted sample, in other words, the diluted sample formed by one uniform mixing process only corresponds to one reactor 20. In this way, the times of uniform mixing to form the diluted sample are increased, thereby reducing the operation efficiency of dilution of the sample, and further influencing the maximum test throughput of the immunity analyzer 10.

However, for the sample dilution method above, the liquid dispensing device 11 uniformly mixes the sample and the diluent in the first reactor so as to form the diluted sample, and dispenses the diluted sample in the first reactor into at least two second reactors. Therefore, the diluted sample each time formed from the uniform mixing by the liquid dispensing device 11 can be used by at least two reactors 20, the liquid dispensing device 11 does not need to perform a separate uniform mixing process for each reactor 20 to form the diluted sample, in other words, the diluted sample formed by one uniform mixing process can correspond to at least two reactors 20, in this way, the times of uniform mixing to form the diluted sample can be greatly reduced, improving the operation efficiency of the sample dilution method, and thus improving the maximum test throughput of the immunity analyzer 10. In particular, for an immunoassay item in which the item to be tested needs to be automatically diluted and then tested, such as test item such as autoimmune diseases or allergen detection, sample dilution is often required, and the diluted sample needs to be subjected to a plurality of tests. For such test items, the sample dilution method effectively addresses the maximum test throughput bottleneck of the immunity analyzer 10.

Figure 5:
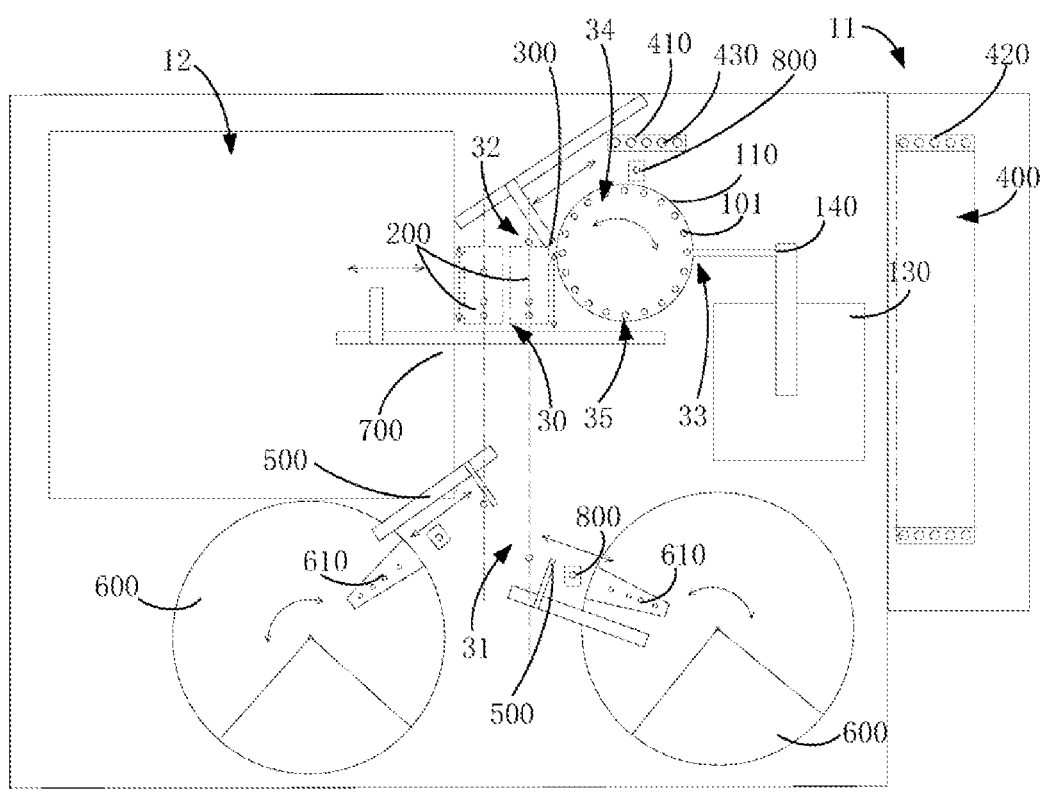
FIG. 5 is a plane structural schematic view of an immunity analyzer provided in a second embodiment.
Figure 12:
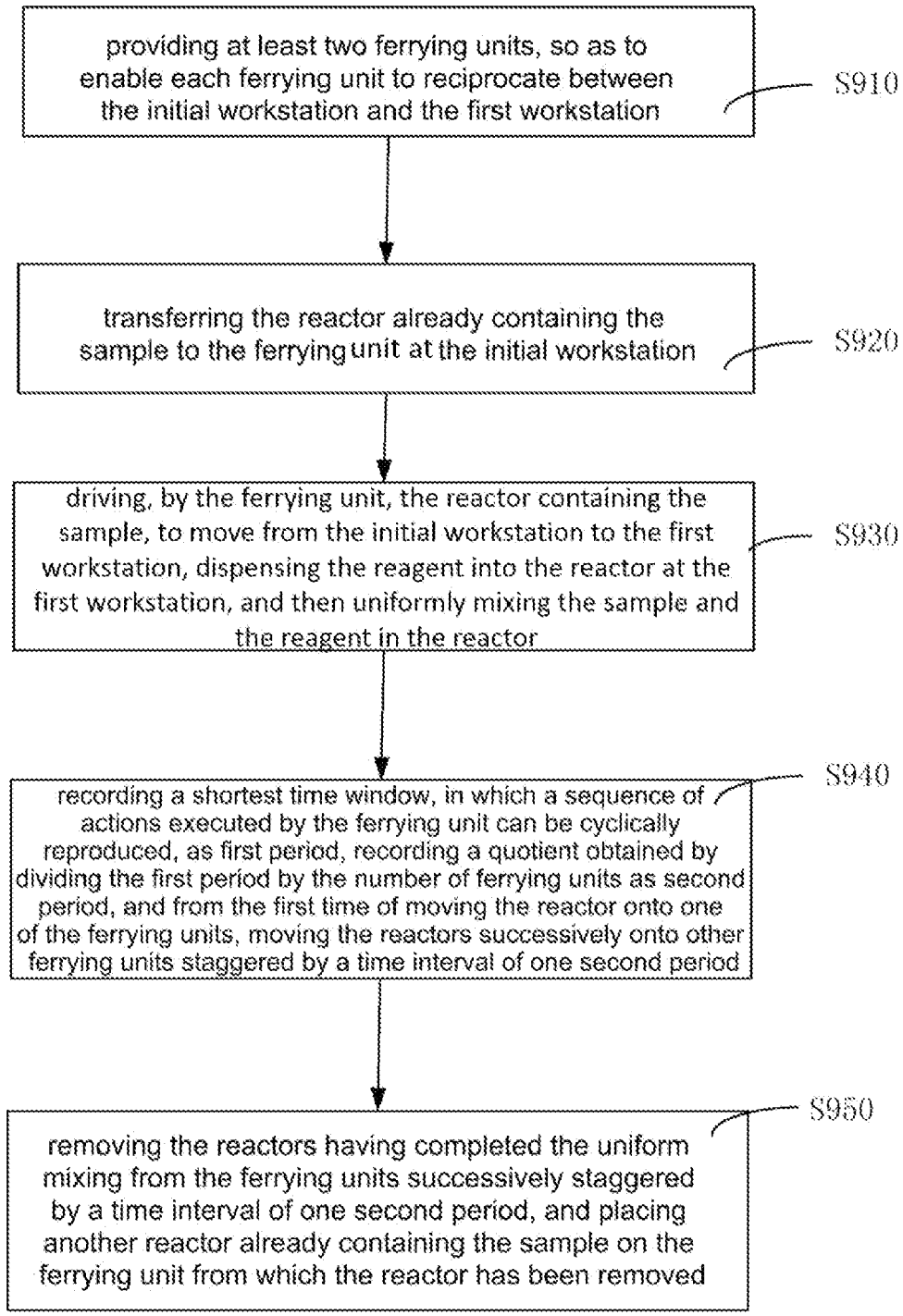
FIG. 12 is a block flowchart of a third liquid dispensing method.

Referring to FIG. 5 and FIG. 12 together, when the number of ferrying units 200 of the above liquid dispensing device 11 is at least two, a third liquid dispensing method may be formed. Certainly, the third liquid dispensing method is similar to the first liquid dispensing method, that is, the sample is not dispensed from the ferrying unit into the reactor 20, but is dispensed from the buffer unit 100 into the reactor 20, and after the sample is dispensed into the reactor 20, the transfer unit transfers the reactor 20 already containing the sample from the buffer unit 100 to the ferrying unit 200. The third liquid dispensing method mainly includes the following steps:

S910, providing at least two ferrying units 200, so as to enable each ferrying unit 200 to reciprocate between the initial position 30 and the first position 31;

S920, transferring the reactor 20 already containing the sample to the ferrying unit 200 at the initial position 30, wherein in fact, the sample is dispensed from the buffer unit 100 into the reactor 20, and after the sample is dispensed into the reactor 20 on the buffer unit 100, the reactor 20 already containing the sample is removed from the buffer unit 100 and moved onto the ferrying unit 200 at the initial position 30;

S930, driving, by the ferrying unit 200, the reactor 20 input from the buffer unit 100 and containing the sample, to move from the initial position 30 to the first position 31, dispensing the reagent into the reactor 20 at the first position 31, and then uniformly mixing the sample and the reagent in the reactor 20;

S940, recording a shortest time window, in which a sequence of actions executed by the ferrying unit 200 can be cyclically reproduced, as first period, recording a quotient obtained by dividing the first period by the number of ferrying units 200 as second period, and from the first time of moving the reactor 20 onto one of the ferrying units 200, moving the reactors 20 successively onto other ferrying units 200 staggered by a time interval of one second period; and S950, removing the reactors 20 having completed the uniform mixing from the ferrying units 200 successively staggered by a time interval of one second period, and placing another reactor 20 already containing the sample on the ferrying unit 200 from which the reactor 20 has been removed.

In order for the whole immunity analyzer 10 to have a higher test throughput, the length of the second period may be any suitable value within 4-15 seconds, such as 4 seconds, 4.5 seconds, 5 seconds, 6 seconds, 9 seconds, and the corresponding test throughput is 900-240 tests per hour, that is, the immunity analyzer 10 may continuously report 900-240 results per hour. For convenience of understanding, the following description is made with the second period being 5 seconds as an example.

Assume that the immunity analyzer 10 must complete a measurement for one reactor 20 every 5 seconds, i.e., report a test result every 5 seconds, in this case, the duration of the second period is 5 seconds. Regarding the whole immunity analyzer 10 as a pipeline, it must be ensured that the flow rates at every place of the pipeline are equal, therefore, the ferrying unit 200 also needs to output a reactor 20 having completed the uniform mixing every 5 seconds. If there is only one ferrying unit 200, since the total time required for the ferrying unit 200 to execute the sequence of actions, such as receiving the reactor 20 already containing the sample, undergoing the reagent dispensing by the reagent dispensing member 500, performing eccentric oscillation to mix uniformly, and removing the reactor 20 having completed the uniform mixing, in one period is greater than 5 seconds, the ferrying unit 200 cannot output one reactor 20 having completed the uniform mixing every 5 seconds, and the flow rate of the ferrying unit 200 is lower than an outlet flow rate of the pipeline, so that the pipeline cannot continuously operate at the maximum efficiency (test throughput). Therefore, by setting the first period to be twice the second period, i.e., the first period is 10 seconds, and meanwhile by setting the number of ferrying units 200 to be two, the sequence of actions executed by two ferrying units 200 is staggered by the duration of the second period (i.e., 5 seconds), i.e., two ferrying units 200 are operated "in parallel in a manner of being staggered" by one second period.

In operation, according to the existing movement law of the ferrying unit 200, assume that the reactor 20 already containing the sample is transferred onto a first ferrying unit 200 at $0^{th}$ second, then the reactor 20 already containing the sample is transferred onto the second ferrying unit 200 at the $5^{th}$ second. Assume that the reactor 20 on the first ferrying unit 200 will be output at the $10^{th}$ second, after the reactor 20 is output, the reactor 20 already containing the sample is transferred onto the first ferrying unit. Then, the reactor 20 on the second ferrying unit 200 will be output at the $15^{th}$ second, likewise, after the reactor 20 is output, the reactor 20 already containing the sample is transferred onto the second ferrying unit. Cyclically running according to the above operation manner will enable the first ferrying unit 200 to output one reactor 20 at $10^{th}$, $20^{th}$, $30^{th}$ . . . $10N^{th}$ seconds; meanwhile, the second ferrying unit 200 will output one reactor 20 at $15^{th}$, $25^{th}$, $35^{th}$ . . . $(5N+10)$th seconds. Therefore, on the basis that each ferrying unit 200 outputs one reactor 20 having completed the uniform mixing every 10 seconds, the two ferrying units 200 as a whole will output one reactor 20 having completed the uniform mixing every 5 seconds, so that the purpose of "exchanging quantity for time" is achieved, and the requirement of the highest test throughput of the immunity analyzer 10 is finally met.

Certainly, when the second period is still 5 seconds, the duration of the first period may also be longer, in which case the number of ferrying units 200 is set to be three, four, or even more, and the first period may be set to be three, four, or even more times the second period, that is, the first period is 15 seconds or 20 seconds, and so on. In this way, on the basis of ensuring the test throughput, the moving speed of the ferrying unit 200 can be reduced, the duration for dispensing the reagent and uniformly mixing the sample and the reagent can be prolonged, then the bottleneck of the moving speed of the ferrying unit 200, the bottleneck of duration of dispensing the reagent and the uniformly mixing the sample and the reagent are effectively solved. In a situation that the moving speed of the ferrying unit 200 and the duration of uniformly mixing the sample and the reagent are fixed, each ferrying unit 200 still outputs one reactor 20 having completed the uniform mixing every 10 seconds, that is, the first period is still 10 seconds.

In the case where the number of storage units 600 of the liquid dispensing device 11 is equal to the number of ferrying units 200, the third liquid dispensing method further includes the following steps:

providing the storage units 600 in the same number as the ferrying units 200, and storing the reagent in a plurality of storage portions 610 of each storage unit 600;

moving the storage portions 610 with the storage units 600 to liquid drawing positions for drawing the reagent; and making the shortest time window, in which the sequence of actions executed by each storage unit 600 can be cyclically reproduced, equal to the first period, wherein from the first time when one of the storage units 600 drives the storage portions 610 to move towards the liquid drawing position, the other storage units 600 are enabled to drive the storage portions 610 to move towards the corresponding liquid drawing positions successively staggered by a time interval of one second period.

With reference to the above relevant description that at least two ferrying units 200 are operated "in parallel in a manner of being staggered" by one second period, by making the number of storage units 600 equal to that of ferrying units 200, and meanwhile making the storage units 600 also operated "in parallel in a manner of being staggered" by one second period, when all the storage units 600 are considered as a whole, the storage portion 610 on one of the storage units 600 is moved to the liquid drawing position every second period, so that the reagent dispensing member 500 draws the reagent at the liquid drawing position. Therefore, for a separate storage unit 600, although the storage portion 610 is driven to move to the liquid drawing position every first period, when all the storage units 600 are considered as a whole, the storage portion 610 arrives at the liquid drawing position every second period, which can also achieve the purpose of "exchanging quantity for time", and the requirement of the highest test throughput of the immunity analyzer 10 is finally met.

In addition, for the conventional solution, the number of storage unit 600 is usually one, and in order to increase the storage capacity of the reagent used for the analytical items, the number of storage portions 610 must be increased, which thus results in an increased size of the whole storage unit 600, then the storage unit 600 occupies a large area, which is not beneficial to the layout and manufacturing of the storage unit 600, and meanwhile, for the storage unit 600 with a large size and weight, the difficulty of controlling the movement thereof is also increased, which results in that the storage portion 610 cannot reach a designated position in a short period of time for the reagent dispensing member 500 to draw the reagent, which becomes a bottleneck in realizing high test throughput. Meanwhile, when the storage unit 600 fails, the whole immunity analyzer 10 cannot operate. By providing at least two storage units 600, with each storage unit 600 having a relatively small volume, the third liquid dispensing scheme is beneficial for the layout and the movement control of the whole machine, and also can ensure a large reagent storage capacity. Meanwhile, the tolerance of the storage unit 600 to fault can be improved, and when one of the storage units 600 fails and cannot operate, the remaining storage units 600 can continue to operate, which ensures that the reagent can be continuously supplied. Certainly, the failed storage unit 600 may be repaired while other storage units 600 are operating.

In some embodiments, the reagent dispensing members 500 are provided in an equal number to that of storage units 600 such that each storage unit 600 corresponds to one reagent dispensing member 500. In this way, the efficiency of dispensing the reagent can be improved, and certainly, the operation efficiency (load) of a single reagent dispensing member 500 can also be reduced on the basis of ensuring the maximum test throughput. The shortest time window, in which the sequence of actions executed by each reagent dispensing member 500 can be cyclically reproduced, is made equal to the first period, and from the time when one of the reagent dispensing members 500 dispenses the reagent, the other reagent dispensing members 500 are made to dispense the reagent successively staggered by the time interval of one second period.

With reference to the above relevant description that at least two ferrying units 200 and at least two storage units 600 are operated "in parallel in a manner of being staggered" by one second period, by making the number of reagent dispensing members 500 equal to that of storage units 600 and that of ferrying units 200, and meanwhile making the reagent dispensing members 500 also operated "in parallel in a manner of being staggered" by one second period, when all the reagent dispensing members 500 are considered as a whole, one of the reagent dispensing members 500 dispenses the reagent every second period, therefore, for a separate reagent dispensing member 500, although it dispenses the reagent into one reactor 20 every first period, when all the reagent dispensing members 500 are considered as a whole, there is a reagent dispensing member 500 to dispense the reagent once every second period, which also can achieve the purpose of "exchanging quantity for time", and the requirement of the highest test throughput of the immunity analyzer 10 is finally met.

When the ferrying unit makes linear movement between the initial position 30 and the first position 31, the storage units 600 may be divided into two halves equal in number, in which one half of the storage units 600 and the other half of the storage units 600 are symmetrical with respect to the movement trajectory of the ferrying unit 200, thus facilitating the layout of the whole immunity analyzer 10.

Therefore, by transferring the reactor 20 already containing the sample to the ferrying unit 200 at the initial position 30, that is, dispensing the sample from the buffer unit 100 in advance into the reactor 20, the time for dispensing the sample from the ferrying unit 200 into the reactor 20 is saved, thus the retention time of the reactor 20 on each ferrying unit 200 is reduced, and each ferrying unit 200 is enabled to quickly output one reactor 20. Meanwhile, at least two ferrying units 200 are provided, and the at least two ferrying units 200 are operated "in parallel in a manner of being staggered" by one second period. Although a single ferrying unit 200 outputs one reactor 20 every first period, all the ferrying units 200, as a whole, will output one reactor 20 every shorter second period, in this way, the purpose of "exchanging quantity for time" can be achieved, and the requirement of the highest test throughput of the immunity analyzer 10 is finally met.

In some embodiments, the third liquid dispensing method is similar to the second liquid dispensing method, that is, the same sample is drawn by the sample adding member 300 and continuously dispensed into at least two reactors 20 on the buffer unit 100, meanwhile, after the same sample is drawn and continuously dispensed into at least two reactors, the sample adding member 300 is washed or replaced. For the beneficial effects thereof, reference can be made to the description of the above second liquid dispensing method.

Likewise, in the process of dispensing the sample, the sample adding member 300 adopts a sample needle or a disposable nozzle, and after the same sample is drawn and continuously dispensed into at least two reactors, the inner wall and the outer wall of the sample needle are washed or the disposable nozzle is replaced. For thorough washing, the duration of washing the sample needle is 2 seconds to 10 seconds. When the capacity of the sample adding member 300 is greater than a total amount of the same sample required for various reactors 20, the sample adding member 300 draws the same sample only once and continuously dispenses the same sample into different reactors 20 in multiple times.

Figure 13:
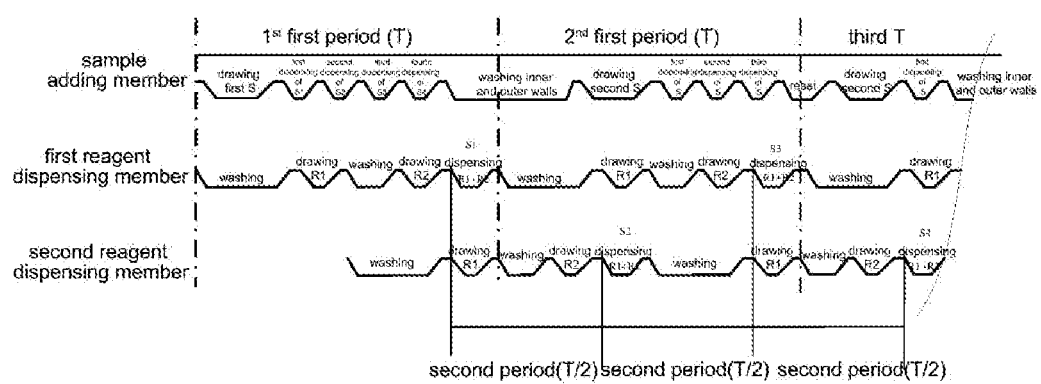
FIG. 13 is a timing diagram of dispensing a sample and a reagent into a reactor in the third liquid dispensing method.

Referring to FIG. 13, testing four analytical items with the same sample (first S) is taken as an example for illustration. The sample adding member 300 draws the same sample (first S) once and continuously dispenses the first S divided into four parts (denoted as S1, S2, S3, S4, respectively) into four reactors in four times. Since the sample drawn by the sample adding member 300 next time is a different sample, after S1, S2, S3, and S4 are dispensed into the four reactors, the inner wall and the outer wall of the sample needle of the sample adding member 300 are washed or the disposable nozzle is replaced.

For the four reactors into which the sample adding member 300 continuously dispenses the sample with one time of drawing, each reagent dispensing member 500 dispenses the reagent corresponding to the analytical item, according to the first period, into the reactor having been dispensed with the first S on the ferrying unit 200 located at the first position, and the two reagent dispensing members 500 dispense the reagent corresponding to the analytical item, at an interval of N second periods, into the reactors having been dispensed with the first S on the ferrying unit 200 located at the first position 31. Specifically, a first reagent dispensing member 500 dispenses the reagent into the first reactor 20 containing S1 in the $1^{st}$ first period T, and dispenses the reagent into a third reactor 20 containing S3 in the $2^{nd}$ first period T, and a second reagent dispensing member 500 dispenses the reagent into the second reactor 20 containing S2 in the $2^{nd}$ first period T, and dispenses the reagent into a fourth reactor 20 containing S4 in the $3^{rd}$ first period T. It can be seen that the first reagent dispensing member 500 and the second reagent dispensing member 500 dispense the reagent corresponding to the analytical item at an interval of N second periods (T/2). In this way, it can be ensured that there is one reactor 20 in each second period (T/2) to complete the dispensing of the reagent, thereby improving the efficiency of dispensing the reagent. In summary, for at least two reactors dispensed with the same sample, each reagent dispensing member 500 dispenses the reagent of the analytical item at intervals of N (N is an integer, N≥I) first periods, successively staggered by one second period (T/2).

The third liquid dispensing method of the present disclosure, on the basis of improving the sample dispensing efficiency and effectively reducing the carryover contamination between the samples, enables at least two ferrying units 200, at least two storage units 600, and at least two reagent dispensing members 500 to efficiently coordinate and move, further improving the efficiency of reagent dispensing and reactant uniform mixing, thus improving the test efficiency and throughput of the immunity analyzer. For example, the test throughput of the immunity analyzer of the present disclosure can break through the highest level (600 tests per hour) currently reported in the industry, and 720, 800 tests per hour or even higher test throughput can be achieved.

The present disclosure further provides an immunoassay method, wherein the immunoassay method includes the steps of the first liquid dispensing method, the second liquid dispensing method, the third liquid dispensing method, and the sample dilution method in the above.

Various technical features in the above embodiments may be combined arbitrarily, and for the sake of concise description, not all possible combinations of the various technical features in the above embodiments are described, while the combinations of these technical features, without conflict, should be considered as within the scope of the present description.

The above embodiments are merely several embodiments of the present disclosure, of which the description is relatively specific and detailed, but they should not be thus construed as limitation on the patent scope of the present disclosure. It should be indicated that a person ordinarily skilled in the art still could make several modifications and improvements without departing from the concept of the present disclosure, all of which fall within the scope of protection of the present disclosure. Therefore, the scope of protection of the present disclosure should be determined by the attached claims.

What is claimed is:

1. A sample dilution method, comprising steps of:
   moving a ferrying unit bearing a first reactor already containing a sample from an initial position to a first workstation;
   dispensing a diluent into the first reactor located at the first workstation;
   uniformly mixing the sample and the diluent in the first reactor so as to form a diluted sample;
   moving the ferrying unit bearing the first reactor containing the diluted sample to a second position, and dispensing the diluted sample in the first reactor located at the second position into at least two empty second reactors;
   moving the ferrying unit bearing the second reactors containing the diluted sample to the first workstation, and dispensing a reagent into the second reactors located at the first workstation; and
   uniformly mixing the diluted sample and the reagent in the second reactors,
   wherein a buffer unit is provided, the first reactor is placed on the buffer unit, and after dispensing the sample into the first reactor on the buffer unit, the first reactor containing the sample is transferred from the buffer unit to the ferrying unit at the initial position, the ferrying unit is configured to make linear reciprocation between the initial position, the first workstation position and the second position, and
   wherein the empty second reactors are placed on the buffer unit, and after the diluted sample is dispensed into the second reactors, the second reactors containing the diluted sample are transferred from the buffer unit to the ferrying unit at the initial position.

2. The sample dilution method according to claim 1, wherein the sample and the diluent in the first reactor and the diluted sample and the reagent in the second reactors are all uniformly mixed by the ferrying unit.

3. The sample dilution method according to claim 2, wherein the uniform mixing is carried out in a manner of non-contact eccentric oscillation.

4. The sample dilution method according to claim 1, wherein the buffer unit is configured to move between a receiving workstation, a sample adding position workstation and a removing position, wherein the first reactor and the second reactors enter the buffer unit from the receiving position, the sample and the diluted sample are dispensed into the first reactor and the second reactors at the sample adding workstation, respectively, and the first reactor and the second reactors all leave the buffer unit and are transferred to the ferrying unit at the removing position.

5. The sample dilution method according to claim 4, wherein the buffer unit is configured to drive the first reactor and the second reactors to make circular movement or linear movement between the receiving position, the sample adding workstation and the removing position.

* * * * *